United States Patent [19]

Matsunaga et al.

[11] Patent Number: 5,958,706
[45] Date of Patent: Sep. 28, 1999

[54] FINE MAGNETIC PARTICLES CONTAINING USEFUL PROTEINS BOUND THERETO, PROCESS FOR PRODUCING THE SAME, AND USE THEREOF

[75] Inventors: Tadashi Matsunaga, B-506, 2-40, Saiwai-cho, Funchi-shi, Tokyo, 183; Shinji Kamiya; Kenryo Namba, both of Tokyo, all of Japan

[73] Assignees: TDK Corporation; Tadashi Matsunaga, both of Tokyo, Japan

[21] Appl. No.: 08/973,275

[22] PCT Filed: Mar. 27, 1997

[86] PCT No.: PCT/JP97/01043

§ 371 Date: Feb. 9, 1998

§ 102(e) Date: Feb. 9, 1998

[87] PCT Pub. No.: WO97/35964

PCT Pub. Date: Oct. 2, 1997

[30] Foreign Application Priority Data

Mar. 28, 1996 [JP] Japan ........................ 8-97536
May 16, 1996 [JP] Japan ........................ 8-146833

[51] Int. Cl.[6] ................ C07K 14/195; C12N 15/31; C12N 15/74; G01N 33/53
[52] U.S. Cl. ................ 435/7.1; 435/320.1; 435/820; 530/350; 530/811; 536/23.7
[58] Field of Search ................ 435/7.1, 7.32, 435/7.7, 7.9, 252.3, 320.1, 820; 436/526, 806, 824; 530/350, 413, 811; 536/23.1, 23.7

[56] References Cited

FOREIGN PATENT DOCUMENTS 62-061584  3/1987  Japan .
2-281142  11/1990  Japan .

OTHER PUBLICATIONS

Nakamura, et al: Iron–Regulated Expression and Membrane Localization of the MagA Protein in Magnetospirillum sp. Strain AMB-1[1], J. Biochem., vol. 118, No. 1, 1995, 23–27 (1995).

Nakamura, et al: An Iron–Regulated Gene, magA, Encoding and Iron Transport protein of Magnetospirillum sp. Strain AMB-1*, The JOuranl of Biological Chemistry, vol. 270, No. 47, pp. 28392–28396.

Primary Examiner—Nancy Degen
Assistant Examiner—Robert Schwartzman
Attorney, Agent, or Firm—Pillsbury Madison & Sutro

[57] ABSTRACT

This invention provides a useful protein-bound magnetic particle which includes a magnetic particle produced in the cell of a magnetic bacterium, and a hybrid protein bound to an organic membrane covering the magnetic particle, and of which the hybrid protein comprises a membrane protein which is originally produced in a state of being bound to the organic membrane, and one or more useful proteins bound biologically through fusion or other binding means to the membrane protein. The protein biologically immobilized does not suffer reduced activity. It is possible to obtain a useful protein such as an enzyme, antibody, etc. immobilized on a magnetic particle, only by cultivating a transformed bacterium, and separating a magnetic particle produced in the cell of the bacterium. When a functional protein is immobilized in this way, it is possible to guide the functional protein magnetically, and to move it to a desired location effectively. As the expression site of a protein can be controlled genetically, a magnetic particle on which a binding protein such as protein A and a labeling protein such as luminescence-related protein are allowed to express themselves close to each other enables a highly sensitive detection process.

26 Claims, 14 Drawing Sheets

Preparation of pKSL

Map of restriction enzyme cleavage sites of pKSL

Preparation of pKSG

Map of restriction enzyme cleavage sites of pKSG

Preparation of pKSA

Map of restriction enzyme cleavage sites of pKSA

Preparation of pNELS

Map of restriction enzyme cleavage sites of pNELS

Preparation of pNELSC

Map of restriction enzyme cleavage sites of pNELSC

Preparation of pNPAML

FINE MAGNETIC PARTICLES CONTAINING USEFUL PROTEINS BOUND THERETO, PROCESS FOR PRODUCING THE SAME, AND USE THEREOF

This application is a 371 of PCT/JP97/01043, filed Mar. 27, 1997.

TECHNICAL FIELD

The present invention relates to protein-bound particles and a production method thereof, as well as a novel protein, gene and so on, and a method for assaying a target substance by the use of the protein-bound magnetic particles.

BACKGROUND ART

Proteins having biological activities such as enzymes and antibodies immobilized on magnetic particles can be led by magnetic means. Therefore, they can be led to local positions at which it has been hitherto difficult for them to reach. Further, they can be collected and separated by means of a magnetic force. Thus they are expected to be utilized in various industries including the fields of medicine and fermentation.

In the prior art, for example, immobilization of biologically active substances to magnetic particles is disclosed in Japanese Patent Publication (KOKOKU) No. 6-12994. Namely, magnetic particles are separated from a magnetic bacterium by an alkaline treatment, and they are further treated with Y-aminopropyltriethoxysilane or glutaraldehyde, and to them a biologically active substance is chemically immobilized. A method is also known, in which magnetic particles are separated by an enzyme treatment from a magnetic bacterium in a state of being covered with an organic thin membrane comprising lipid, and a protein is immobilized thereto after a treatment with glutaraldehyde. A method is also known in which a biologically active substance is immobilized on magnetic particles by a chemical binding method using SPDP (Japanese Pre-examination Patent Publication (KOKAI) No. 5-209884).

Further, methods for measuring antigens or antibodies have been proposed, in which an antigen-antibody reaction is allowed to occur by way of the magnetic particles to which a biologically active substance has been chemically immobilized by the aforementioned methods (Japanese Pre-examination Patent Publication (KOKAI) Nos. 4-285857, 5-209884, and 5-99926).

However, in any of the foregoings, it is necessary for a protein such as an enzyme of an antibody, etc. to be chemically bound, to magnetic particles. Thus poblems have arisen: a long time is required for the immobilization treatment; the biological activity of the protein is impaired; the amount of immobilized protein is greatly dispersed from one lot to another, and its biological activity is also greatly dispersed from one lot to another; and the immobilized protein inevitably becomes expensive because the protein to be used for immobilization is generally expensive.

Further, the aforementioned method in which labeled antibodies have been bound to magnetic particles before use makes it necessary that, in advance, a labeling substance is chemically bound or physically adsorbed to the antibodies. Because of this, the antibodies may lose its activity, or lose its fraction due to the treatment. Furthermore, the amount and binding mode of the labeling substance immobilized to the magnetic particles may vary, causing a variation in measurement data, which may, in turn, lead to an increased cost.

Accordingly, an object of this invention is to overcome the problems accompanying the conventional techniques in which an enzyme, antibody or labeling compound is immobilized to magnetic particles by a chemical method, and to provide a method enabling a high sensitivity measurement of a target substance, and magnetic particles to be used in that method.

DISCLOSURE OF INVENTION

Useful protein-bound magnetic particles

The first aspect of this invention consists in providing a useful protein-bound magnetic particle which comprises: a magnetic particle which is produced in the cell of a magnetic bacterium, and a hybrid protein bound to an organic membrane covering the magnetic particle; said hybrid protein comprising a polypeptide chain containing at least a membrane-bound portion of a membrane protein which is originally produced in a state of being bound to the organic membrane and at least one other protein which is biologically bound to said polypeptide.

BEST MODE OF CARRYING OUT THE INVENTION

Figure 1:
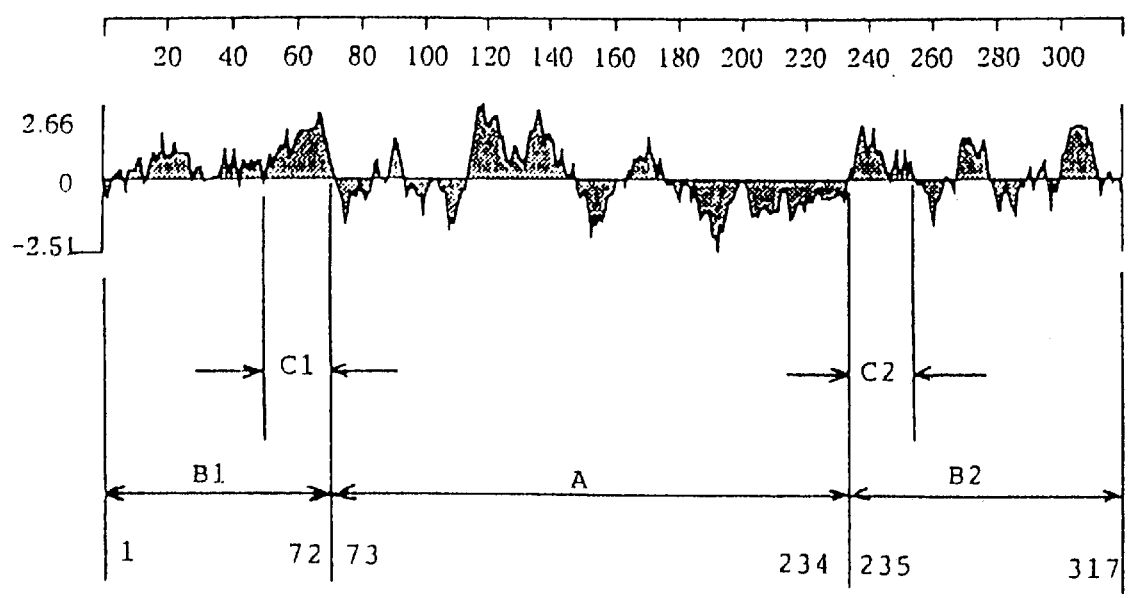
FIG. 1 is a chart representing hydrophilic-hydrophobic regions of the amino-acid sequence of the mps protein obtained through the analysis by Kyte-doolittle method.

The magnetic particles used in this invention are the particles composed of magnetites with a diameter of 50–150 nm which are produced in the cell of a magnetic bacterium. The usable magnetic bacterium includes, for example, microorganisms of the genus Magnetospirillum (e.g., bacterial strains AMB-1 (FERM BP-5458), MS-1 (IFO 15272, ATCC 31632, DSM 3856) and SR-1 (IFO 15272, DSM 6361) and of the genus Desulfovibrio (e.g., RS-1 (FERM P-13283)).

The magnetic particles produced in the cell of those magnetic bacteria are covered with an organic membrane composed mainly of phospholipids. To that organic membrane are bound various membrane proteins. The membrane protein to be used in this invention is preferably comparatively firmly bound to the membrane and its part or parts are exposed to space outside the membrane. Particularly preferably, it has both terminal ends exposed to the outside space. The exposed part(s) of the membrane protein is utilized as a means through which a useful protein is immobilized with respect to the organic membrane. The exposed part(s) is used in order that a useful protein is bound to the membrane protein.

The binding of the useful protein to a polypeptide chain occurs as a result of a biological binding. The "biological binding" here includes not only a bond which occurs between two different proteins which are united through fusion into a polypeptide, but also a bond by way of an antigen-antibody reaction, ligand-receptor reaction, etc.

The appropriate bonding type includes followings. The bonding type may be chosen as appropriate depending on the kind of the membrane protein to be used as a means for immobilization.

(a) A bonding type in which a kind of useful protein is biologically bound to one end of a polypeptide chain which contains a membrane bound portion.

(b) A type in which two kinds of useful protein are separately bound to the different ends of a polypeptide chain which contains a membrane bound portion.

(c) A bonding type in which, of two kinds of useful protein, one kind is biologically bound to one end of a polypeptide chain which contains a membrane bound portion, and the other kind is bound in series to the other end of the foregoing protein which has been bound to the polypeptide chain. The sequence of binding of the two useful proteins may be appropriately determined according to the nature of the proteins.

In any of above bonding types (a) to (c), the bonding between different proteins can take place through a biological binding directly, or indirectly by way of a crosslink of a third protein. As a still other bonding type which is derived by combining (b) and (c), three or more useful proteins may be involved in the bonding.

"A polypeptide chain containing at least a membrane-bound portion of a membrane protein", quoted above may include only the amino-acid sequence corresponding to the membrane bound portion, or other amino-acid sequences which comprise, besides the above amino-acid sequence, amino-acid sequences derived from, or not derived from the membrane protein.

Production of useful protein-bound magnetic particles

The aforementioned useful protein-bound magnetic particles can be produced by the use of transformed magnetic bacteria.

Namely, the second aspect of this invention consists in providing a method for producing a useful protein-bound magnetic particle as described above which comprises: cultivating a magnetic bacterium transformed with a plasmid which contains a fusion DNA sequence resulting from the fusion of a gene fragment coding at least for a membrane-bound portion of a membrane protein which is originally produced in a state of being bound to the organic membrane, and a DNA sequence coding for said useful protein, to thereby make said fusion DNA sequence express; thus producing a fusion protein containing said useful protein in a state of being bound to the organic membrane covering the magnetic particle in the cell of said bacterium.

The transformation of the magnetic bacterium with the recombinant plasmid can take place by known methods. The magnetic bacterium to be used as a host includes the strains mentioned above.

The magnetic bacterium thus transformed, when cultured under a proper condition, generates in its inferior the desired useful protein in a state of being fused to a polypeptide chain which contains the membrane bound portion of a membrane bound protein. The fused protein is bound to the organic membrane covering the magnetic particles.

The magnetic particles to which the useful protein has been bound can be collected easily through magnestism, after the magnetic bacteria have been allowed to proliferate through cultivation, and their cell bodies have been ground or lysed by a conventional method.

The magnetic bacterium which is the source of a membrane protein used to immobilize a useful protein according to this invention, and the magnetic bacterium which serves as a host for the recombinant plasmid may belong to the same species or different species.

Generally speaking, any membrane proteins can be used in the present method for producing useful protein-bound magnetic particles, as long as they are firmly bound to an organic membrane covering magnetic particles in the cell of the magnetic bacterium, and preferably their parts are exposed to space outside the organic membrane. If only a gene is known which codes at least for the membrane-bound portion of a membrane protein, it is possible to produce magnetic particles to which a useful protein has been bound in the cell of a magnetic bacterium, by preparing, by a known method, a recombinant plasmid which contains a fused DNA sequence containing the gene fragment and one or more DNA sequences coding for one or more desired useful proteins, transforming an appropriate magnetic bacterium with that recombinant plasmid, and then cultivating the transformed magnetic bacterium thus obtained.

The present inventors have found, as representative examples of the membrane protein to be used in the manner described above in this invention, proteins mps and magA which are produced by the magnetic bacterium AMB-1 (FERM BP-5458).

[Information regarding deposition of the magnetic bacterium AMB-1]

Deposited organization

Name: National Institute of Bioscience and Human-Technology, Agency of Industrial Science and Technology Address: 1–3, Higashi 1-chome, Tsukuba-shi, Ibaraki-ken 305, Japan Date of deposition: November 12, 1992

Deposition No.: FERM BP-5458

The present invention is described specifically using these proteins and genes coding for the proteins as examples.

[Utilization of mps protein]

mps protein is an isolated and purified protein which has the amino-acid sequence as depicted by SEQ ID NO: 1 in Sequence Listing described below (together with the base sequence of the corresponding structural gene).

This protein was isolated and purified as follows. The magnetic bacterium AMB-1 was cultured until it entered into a stationary phase. The cells were collected by centrifugation, and disrupted using a French press. From the cell disrupted suspension was separated a cell membrane fraction, and a magnetic particle fraction was separated with a samarium cobalt magnet for purification. Then, the fraction was put into a 1% Tryton 10 mM Tris buffer solution, and was stirred for two hours to separate magnetic particles from organic membranes. The extract obtained after above treatment was submitted to protein electrophoresis (SDS-PAGE). When the electrophoretic pattern thus obtained was compared with that from the proteins existent on the cell membrane, three spots were found to be specific to an organic membrane which was not present on the cell membrane. Of the three proteins existent on the organic membrane, the protein which is most abundantly contained in the sample was termed as mps protein. The band representing this mps protein was found to correspond with a below-described protein of a molecular weight of 34.49 kDa encoded by mps structural gene.

Of the amino-acid sequence of this mps protein, the distribution of hydrophilic and hydrophobic regions was examined by Kyte-doolittle method, and the result is shown in FIG. 1. From this it was found that the central range from 73rd to 234th amino acid residues as counted from the N-terminal (region A in FIG. 1) is comparatively high in hydrophobic activity and is involved in the binding to the organic membrane, while the region from 1st to 72nd amino acid residues adjacent to the N-terminal and the region from 235th to 317th amino acid residues adjacent to the C-terminal are comparatively high in hydrophilic activity, and are for the most part exposed to space outside the membrane. The central range from 73rd to 234th amino acid residues is a membrane-bound portion.

mps structural gene:

Said mps protein is encoded by mps structural gene.

The mps structural gene consists of the DNA sequence whose base sequence is as depicted in SEQ ID NO: 3 in Sequence Listing described below.

A gene fragment represented by SEQ ID NO: 3 in Sequence Listing, as the mps structural gene, was isolated and purified from the magnetic bacterium AMB-1 as follows.

mps protein isolated as above was analyzed of its amino-acid sequence by Edman's decomposition method, and the amino-acid sequence of its N-terminal was determined. A primer was prepared from the N terminal amino-acid sequence, and a gene fragment coding for N-terminal of mps protein present only on the organic membrane was cloned by PCR. With the gene fragment as a base, gene walking was employed, and about 2 kb of sph I fragment adjacent to that gene fragment was cloned. The gene fragment was sequenced, the sequence of mps structural gene with 945 kb was determined, and the aforementioned amino-acid sequence was deduced from the sequence of that gene.

Within a range of about 700 nucleotides upstream from the mps structural gene sequence, there is a promoter. However, any other known promoter can be used instead.

Of the mps structural gene, the DNA sequence coding for the membrane bound portion is the range of from 217th to 702nd bases of the sequences as depicted in SEQ ID NOS: 2 and 3. In the method whereby useful protein-bound magnetic particles are produced, a gene fragment containing at least the DNA sequence of this range (hereinafter, referred to as "gene fragment for membrane-bound portion", because it codes for a polypeptide chain containing the membrane-bound portion of the membrane protein described above) is used to be fused with another DNA sequence coding for a desired useful protein. For the present purpose, the gene fragment for the membrane-bound portion may consist only of the DNA sequence which codes for the membrane-bound portion, or may comprise the same DNA sequence whose 3' or 5' terminal is flanked with another DNA sequence which is, or is not, originally present in mps structural gene. A part or the whole of DNA sequence that is originally present in mps structural gene may be allowed to exist intact. It is rather advantageous that a DNA sequence coding for a part comparatively high in hydrophilic activity and to be exposed to space outside the membrane is allowed to coexist, because then the useful protein to be bound to the membrane-bound protein is to be expressed as a substance exposed to space outside the organic membrane. Namely, it is preferable that, outside A region in FIG. 1, there exist DNA sequences coding at least for a part of B1 region (ranging from 1st to 216th base), and/or, at least a part of B2 region (ranging from 703rd to 951st base), or more specifically, C1 region (ranging from 154th to 216th base) and/or C2 region (ranging from 703rd to 768th base).

The gene fragment for membrane-bound portion must include the gene coding for the membrane-bound portion of the membrane-bound protein as an essential element, and may consist only of that gene, but, as mentioned above, it may be flanked at its 3' or 5' terminal with other base sequences which are originally present in mps structural gene. Or, the gene fragment in question may be flanked at either or both of its 3' and 5' terminals with other DNA sequences which are so artificially extended as to give appropriate sites that are cleaved by a restriction enzyme. This gene fragment for membrane-bound portion plays an important role because in expression of the membrane-bound portion which acts as a means to immobilize the useful protein onto the organic membrane.

[Utilization of magA protein]

The amino-acid sequence of mag A protein is as depicted in SEQ ID NO: 4 in Sequence Listing described below (together with the corresponding base sequence of mag A gene). It includes a hydrophilic region in a range of 1st to 6th amino-acid residues as counted from N-terminal, a hydrophobic region in a range of 7th to 380th amino-acid residues subsequent to above, and a second hydrophilic region in a range of 381st to 434th amino-acid residues subsequent to the foregoing. The central, long hydrophobic region is a portion to be bound to the membrane, and the hydrophilic regions of both ends are exposed to space outside the organic membrane. To be more specific, the hydrophobic region contains about four short, hydrophilic parts, and the parts are presumably exposed to space outside the organic membrane. The hydrophobic region of mag A protein acts as a means to bind that protein to the organic membrane covering magnetic particles, and the hydrophilic regions at both ends of the protein are exposed to space outside the organic membrane. The hydrophobic region is the membrane-bound portion of mag A protein.

The mag A protein was isolated and purified as follows. The magnetic bacterium AMB-1 was cultured until it entered into a stationary phase. The cells were collected by centrifugation, and disrupted using a French press. From the cell disrupted suspension were separated magnetic particles with a samarium cobalt magnet, and purified. Then, the magnetic particles were put into a 1% Tryton 10 mM Tris buffer solution, and stirred for two hours to separate magnetic particles from organic membranes. The extract obtained after above treatment was submitted to protein electrophoresis (SDS-PAGE). A band was confirmed to appear at a location indicating 46.8 kDa which is equal to the molecular weight known as that of the protein encoded by the below-described magA structural gene.

The present inventors have found that the gene coding for this magA protein referred to as (mag A structural gene) has a DNA sequence as depicted in SEQ ID NO: 5 in Sequence Listing described below. A promoter is upstream and adjacent to the sequence of mag A gene (J. Biochem. 118, 23–27 (1995)). Mag A protein is generally encoded by the base sequence as depicted in SEQ ID NO: 6.

The mag A gene represented by SEQ ID NO: 5 was found in the magnetic bacterium AMB-1, isolated and purified in the manner as described below.

Figure 2:
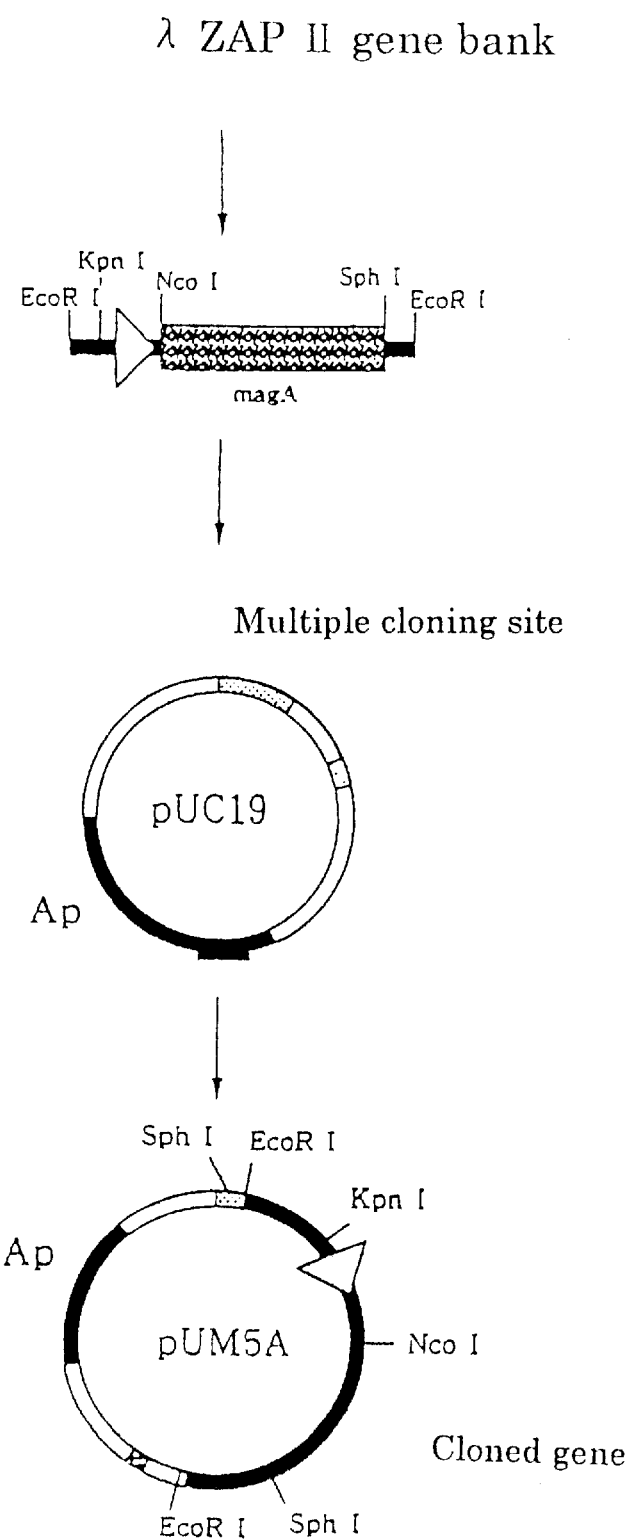
FIG. 2 illustrates the preparation of plasmid pUM5A, and presents a map of restriction enzyme cleavage sites of the same plasmid.

A transposon Tn5 or a transposable gene with a drug resistance factor (Km) was introduced into the magnetic bacterium AMB-1 to cause non-specific mutations in its genome in terms of mutation sites, and thereby to produce a mutant which lacks a property to produce magnetic particles. Then, with the presence of drug resistance factor (Km) as a marker, bacterial cells unresponsive to magnetism were separated, and genomes were extracted from those mutants. The genome, after being cleaved by EcoRI, was submitted to southern hybridization, and gene fragments containing mag A genes were isolated according to whether they had hybridized with the transposon Tn5, and purified through cloning by way of pUC19. A plasmid pUM5A prepared here is shown in FIG. 2. As a result of gene analysis, it was found that it contained a mag A gene of 1.3 kb in length.

The DNA sequence coding for the membrane-bound portion of the mag A structural gene corresponds to the range from 19th to 1140th base of SEQ ID NO: 4 in Sequence Listing mentioned above. In the aforementioned method for producing useful protein-bound magnetic particles, a gene fragment containing at least this range of DNA sequence (gene fragment for membrane-bound portion) is used for fusion with a DNA sequence coding for a desired, useful protein. In this case also, the gene fragment for membrane-bound portion may consist only of the gene segment coding for the membrane-bound portion of mag A protein, or may include, in addition, a part or whole of the gene coding for the hydrophilic region. The gene fragment for membrane-bound portion is not limited to any specific sequence as long as it contains the gene coding for the membrane-bound portion, and a DNA sequence generated at the fused part with a DNA sequence coding for a useful protein is suitable for the synthesis of amino acids. The DNA sequence coding for the useful protein may be inserted into a position adjacent to the DNA sequence coding for the membrane-bound portion, or a part of the DNA sequence coding for the hydrophilic region may be inserted between the DNA sequence coding for the hydrophobic region and the DNA sequence coding for the membrane-bound portion. Further, the gene fragment for membrane-bound portion may have, at either or both of its terminals, an artificial extension of DNA sequence which has appropriate sites to be cleaved by a restriction enzyme. Particularly, as the DNA sequence coding for the hydrophilic region on the side of 5' terminal has a short length, it may be included as a whole, or parts of its length may be added as appropriate. As for the sites at which the DNA sequence coding for the desired, useful protein can be inserted, the restriction enzyme cleavage sites on the functional 5' terminal include a Sca I cleavage site which have been introduced into the mag A gene, while the restriction enzyme cleavage sites on 3' terminal include Sph I and Dra III cleavage sites. Sph I and Dra III cleavage sites are among convenient locations for cleavage, because they are at a stretch coding for a hydrophilic region slightly shifted downstream from the DNA sequence coding for the hydrophobic region of mag A gene.

[Fusion DNA sequence]

A fusion DNA sequence of (a) a gene fragment for membrane-bound portion which codes for a polypeptide chain containing at least the membrane-bound portion of a membrane protein such as mps protein or mag A protein, and (b) one or more, desired useful proteins, is prepared.

The DNA sequences coding for one or more, useful proteins may fuse with either or both of 3' and 5' terminals of the gene fragment for membrane bound portion. When it is allowed to fuse with both terminals of the gene fragment in question, one introduced at 3' terminal may encode the same protein as or a different protein from what the other at 5' terminal encodes. Advantages characteristic with fusion at both terminals can be obtained in following cases.

1) Introduction of two DNA sequences coding for the same protein at both terminals will increase the amount of the same protein immobilized on magnetic particles.
2) Introduction of two DNA sequences coding for proteins which constitute two cascade elements of a complex enzyme system, or a combination of enzyme and coenzyme or reproductive enzyme, at 5' and 3' terminals will help to accelerate the reaction of the enzyme system.
3) Introduction of two DNA sequences coding for proteins forming subunits of a mother protein at 5' and 3' terminals will help to accelerate the formation of those subunits towards the completion of the mother protein.

Two or more DNA sequences coding for two or more proteins may be fused with either or 5' and 3' terminals one after another in a series.

Fusion genes coding for different proteins are not limited to any specific kinds.

[Recombinant plasmid]

The transformed magnetic bacterium which produces useful protein-bound magnetic particles of this invention has been transformed by a recombinant plasmid containing the fusion DNA sequence above.

The recombinant plasmid can be obtained after the fusion DNA has been introduced into an appropriate vector plasmid by a known method.

The vector to be used for the preparation of the recombinant plasmid includes, for example, pRK415 and pKT230 strains. The gene is introduced into a chosen vector. The order to introduction of the gene and a restriction enzyme to be used are determined such that the vector may grow most efficiently, and the gene may have a desired orientation. After the procedure for introduction of the gene has been determined, the DNA sequence is cleaved by the restriction enzyme, and the yield is subject to electrophoresis to separate the desired gene fragments to be introduced. Later, the gene fragments are connected together through ligation by a ligase. When the connection parts of the gene fragments do not fit together, their terminals are subject to a flattening treatment and then to ligation. Restriction enzymes, ligases and enzymes for terminal flattening all can be obtained from commercially available products. Lastly, the cleavage pattern due to the restriction enzyme is checked to see whether a desired plasmid is obtained or not.

[Transformed magnetic bacterium]

Transformation of a magnetic bacterium by the plasmid above can be performed by a known method. The magnetic bacterium to serve as a host may be the same as the bacterium which acts as a source of the membrane protein to be used, or may be different from the latter, but it is preferably the same with the latter. The usable magnetic bacterium includes AMB-1 as a representative species, but is not limited to it, and may include, for example, microorganisms of the genus Magnetospirillum (e.g., bacterial strains AMB-1 (FERM BP-5458), MS-1 (IFO 15272, ATCC 31632, DSM 3856) and SR-1 (IFO 15272 DSM 6361) and of the genus Desulfovibrio (e.g., RS-1 (FERM P-13283)).

The magnetic bacterium thus obtained is allowed to grow under an optimum condition, to produce magnetic particles in its interior which have a desired, useful protein. To be more specific, the desired protein is produced, in a state of being fused with a polypeptide chain encoded by a gene fragment for a membrane-bound portion of protein, and being bound to an organic membrane covering the magnetic particles. The useful protein-bound magnetic particles thus produced is readily collected by magnetism after the cell bodies of proliferating magnetic bacteria have been ground to pieces and dissolved by a known method.

Further, the aforementioned method for producing a useful protein is also useful for the production of a useful protein whose isolation and purification are not amenable to a conventional method, even though it has no functionality. In this case, the useful protein is obtained in a state of being bound to magnetic particles, but it can be easily isolated from other cellular components by a magnetic means such as the use of a magnet, and then be purified.

In this invention, the gene coding for the useful protein which is fused with the gene for the membrane-bound portion of membrane protein and the protein expressed by that gene are not limited to any specific kinds. When such protein is used in medicine or in industries incorporating fermentation, it may be conferred a certain function, for example, it may be a protein with a physiological activity. However, it is not limited to above, and the present method can be applied for the production of a protein, isolation and extraction of which is scarcely amenable to a conventional method. The protein, being produced in the form of a fusion protein on magnetic particles, can be easily separated and collected by a magnetic means.

Among useful proteins, the functional protein includes, for example, immunity-related proteins such as an antigen, antibody, protein A, etc., proteins with a binding activity such as lectin, avidin, etc., enzymes such as a coenzyme, hydrolysis enzyme, oxidation-reduction enzyme, catalase, transferase, elimination enzyme, restriction enzyme, etc.

Further, the aforementioned method for producing a useful protein is also convenient for the production of a useful protein whose isolation and purification are not amenable to a conventional method, in spite of its having no functionality. In this case, the useful protein is obtained being bound to magnetic particles, but it can be easily isolated from other cellular components by a magnetic means such as the use of a magnet, and then purified.

Magnetic particles to which a binding protein and a labeling protein are bound

This invention also provides, as one embodiment of the aforementioned useful protein-bound magnetic particles, magnetic particles to which as useful proteins, a binding protein and a labeling protein are bound, and a method for measuring a target substance based on the use of those magnetic particles.

Namely, this invention provides magnetic particles to which a binding protein and a labeling protein have been bound wherein the binding protein and labeling protein are bounded close to each other through a biological bond to a polypeptide chain which contains at least a membrane-bound portion of a membrane protein which is produced in the cell of a magnetic bacterium, in a state of being bound to an organic membrane covering the magnetic particles.

Quantification or a target substance

This invention further provides a method for assaying a target substance in a sample which comprises:

(A) adding magnetic particles to which are bound a binding protein which binds specifically to the target substance and a labeling protein, to the sample, so that, if the target substance is present at all in the sample, it may react with that binding protein to cause magnetic particles to aggregate;

(B) next, measuring signals based on the existence of the labeling protein after aggregation; and (C) comparing the thus obtained intensity of signal with that from a standard sample, to quantify the target substance in the sample, characterized in that:

the binding protein and labeling protein are bound close to each other through a biological bond to a polypeptide chain which contains at least a membrane-bound portion or a membrane protein produced in a state of being bound to an organic membrane covering the magnetic particle which is produced in the cell of a magnetic bacterium.

In the aforementioned method, as aggregation proceeds according to the amount of the target substance in the sample, the labeled protein bound to the magnetic particles loses its function mainly because of physical hindrance (steric hindrance). Accordingly, a signal derived from the target protein declines in proportion to the aggregated amount of magnetic particles or the reaction amount of the target substance. Therefore, if, for example, the target protein is an enzyme to mediate a luminescence reaction, the luminescence intensity will decrease. Thus, measurement of the luminescence intensity by an optical means allows detection or determination of the target substance in the sample. The aggregation reaction can be readily stimulated after reaction, for example, through the application of an alternating magnetic field.

[Magnetic particles to which a functional protein is bound]

To be specific, binding of a binding protein and a labeling protein may take place, for example, in following modes. An appropriate binding mode may be chosen from them according to the kind of a protein which is used as an immobilizing means.

(a) A mode where a binding protein and a labeling protein are bound separately to different terminals of a polypeptide chain. In this mode, binding of the functional proteins, that is, the binding protein and the labeling protein, to the polypeptide chain may take place through direct fusion, or by way of a third protein fused with the terminal of the polypeptide chain to which the functional protein may then be bound through a biological bond.

(b) Another mode where one of the two functional proteins, that is, the binding protein or the labeling protein is fused with one terminal of the polypeptide chain, and the other functional protein is fused in series with the opposite end of the former functional protein. The order of binding of the binding and labeling proteins may be determined as appropriate according to the kinds of proteins used.

Either of (a) and (b) requires preparation of a fusion protein of a polypeptide chain containing a portion to be bound to the organic membrane, and functional proteins or the like. This is achieved by preparing a recombinant plasmid containing corresponding fusion DNA sequences, cultivating magnetic bacteria transformed with the recombinant plasmid to express the fusion DNA sequences, to produce, in the cell bodies of bacteria, the fusion proteins containing the required functional proteins in a state of being bound to an organic membrane covering magnetic particles. Thus, magnetic particles to be used in the aforementioned method are obtained.

In the aforementioned magnetic particles, a binding protein and a target protein are bound "close to each other" to a polypeptide chain. "Being close to each other" means here that there is no other peptide between the two proteins, or only 1–1000 peptides intervene between the two. If there is a peptide between the two proteins, it is required that the two proteins do not lower its activity owing to steric hindrance, and that the third protein bound to the binding protein does not lower its activity.

[Target substance]

The target substance which can be assayed by the above method may include any substances, as long as a binding protein is available which is capable of binding specifically to that target substance. The specific binding is not limited to any particular mode, and includes, for example, antigen-antibody reaction, ligand-receptor reaction, or the like.

Accordingly, the target substance which can be quantified by the above method includes, for example, antigens, antibodies, substances capable of binding to a protein as a ligand, (substrates capable of binding to an enzyme, co-enzymes, a regulatory factor; lectins capable of binding to receptor, hormones, neurotransmitters, etc.), either of protein A and antibody, polysaccharides/complex carbohydrates capable of binding to a lectin, biotins capable of binding to avidins such as avidin, streptoavidin, etc. It is known that various substances including antibodies, animal and plant cells, bacteria, viruses, etc. can act as an antigen, and thus are amenable to quantification by the method of this invention.

[Binding protein]

The binding protein which is bound to magnetic particles is capable of specifically binding to the target substance in a sample.

The binding protein is selected according to the target substance above, and includes, for example, proteins which act as an antigen or antibody, proteins capable of binding to the aforementioned ligands, the remaining one of a pair of protein A and antibody, other immunity-related proteins, lectins, avidins, etc.

[Labeling protein]

The labeling protein or a functional protein to generate a signal for detection in the aforementioned method includes, for example, fluorescent proteins such as green fluorescence protein, fluorescent dye-bound proteins, luminescence-related enzymes involved in biological or chemical luminescence reactions and amenable to quantification by an optical means such as luciferase, alkaline phosphatase, peroxidase, β-D-galactocidase, glucose oxidase, glucose-6-phosphate dehydrogenase, etc., and enzymes whose activity is measured in a separate assay, such as coenzymes, hydroxylase, oxidation-reduction enzymes, isomerase, transferase, elimination enzymes, restriction enzymes, etc. The former is more preferable because they are amenable to quantification by an optical means.

EXAMPLES

Example 1

I. Preparation of recombinant plasmids

Figure 3:
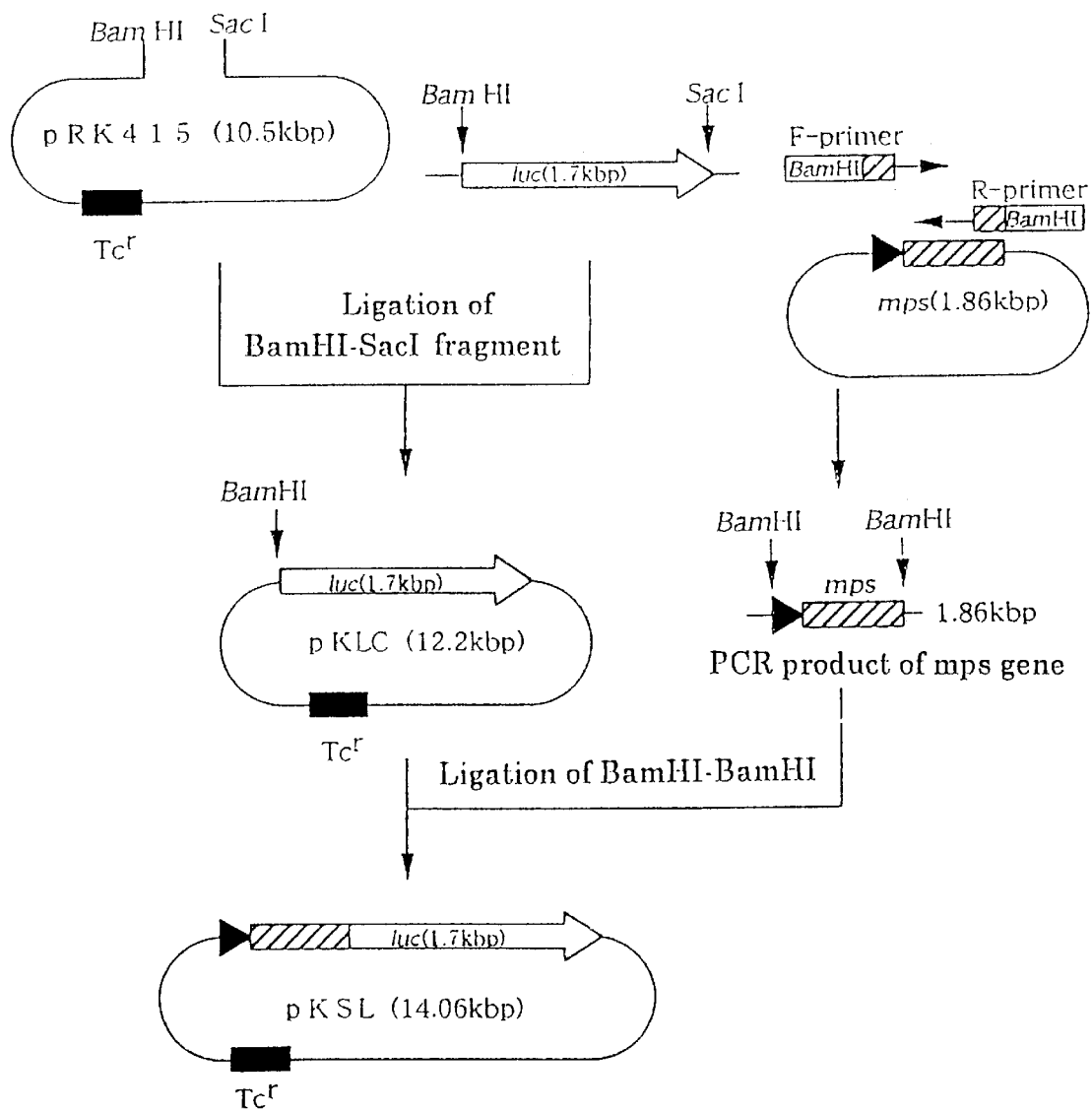
FIG. 3 illustrates the method of preparation of plasmids pKLC and pKSL prepared in Example 1.

In order to express a firefly luciferase gene (luc gene, produced by Toyo ink) in a magnetic bacterium, and produce a luminescent protein encoded by the gene on an organic membrane covering magnetic particles, a plasmid pKSL ligated with a mps-luc fusion gene was prepared in accordance with the method shown in FIG. 3.

A plasmid pRK415 (N. T. Neen, S. Tamaki, D. Kobayashi, and D. Trallinger, 1988, Gene 70:191–197) which can introduce a gene through conjugative transfer into the magnetic bacterium AMB-1, and has a tetracycline resistance gene was used as a vector. pRK415 was digested by Bam HI and Sac I, into which was introduced a luc gene which had been digested by Bam HI and Sac I, to produce the plasmid pKLC. Further, the plasmid pKLC was digested at a Bam HI on the upstream end of the luc gene.

Figure 4:
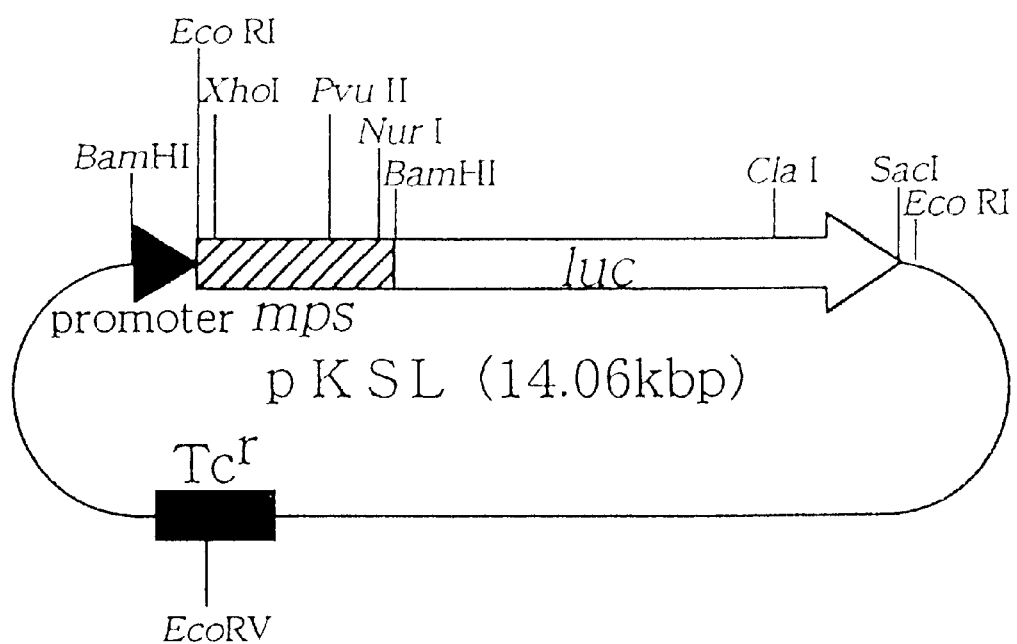
FIG. 4 is a map of restriction enzyme cleavage sites of the plasmid pKLC.

Next, by PCR using an F-primer which has a sequence complementary to 5' terminal part of a DNA sequence containing the mps structural gene and a promoter segment upstream thereof and has been designed for a Bam HI recognition site, and an R-primer which has a sequence complementary to 3' terminal part of the same DNA sequence and has been designed for a Bam HI recognition site, application was effected, to produce a binding DNA sequence having Bam HI recognition sites at both ends. The thus amplified binding DNA sequence was ligated with the plasmid pKLC to produce a plasmid pKSL. The restriction enzyme cleavage map of pKSL is shown in FIG. 4. Above procedures allow the luc gene to be translated without causing any shift from the reading frame of the mps structural gene, to produce a fusion protein.

II. Preparation of transconjugants

Next, the recombinant plasmid obtained in I. was introduced through electroporation into E. coli S17-1, and then transferred through conjugative transfer into a wild strain AMB-1, to produce a transconjugant. Because E. coli S17-1 serving as a host bacterium during conjugative transfer has a tra gene, it can achieve conjugative transfer without requiring a helper plasmid. For conjugative transfer, magnetic bacteria grown on MSGM medium to a middle to late logarithmic phase with a density of about $8 \times 10^7$ cells/ml were used. One day before, the plasmids were introduced into the host bacteria, and developed colonies were scraped off and suspended in a density of $10^9$–$10^{10}$ cells/ml. The two kinds of bacteria were mixed at a ratio of 1:50 (magnetic bacteria: E. coli), and the mixture was spotted on an agar plate to allow mating. Six hours later, the spot was cut out with a scalpel, and bacterial cells were recovered using about 5 ml of MSGM medium. The suspension was inoculated onto an MSGM medium added with 2.5 μg/ml of tetracycline. Incubation was carried out at 25° C. to allow proliferating cells to transform into transconjugantes. In this incubation, E. coli does not grow on this MSGM medium.

Next, magnetic particles were separated from the magnetic bacteria which had been cultured on the MSGM medium after the conjugative transfer. The magnetic bacteria, after being collected by centrifugation, were washed twice with 10 mM Tris buffer, and suspended to give a concentration of not more than 0.1 g cell/ml, followed by supersonic disruption treatment, in which supersonic disruption under the conditions of an output of 120 W and a duration of 30 sec was repeated five times. While the cell-disrupted suspension contained in a vessel was cooled with ice, an Sm—Co magnet was applied on the external wall of the vessel for 30 minutes, to separate magnetic particles in the suspension. The suspension was further centrifuged at 5,000 G for 15 minutes for separation of a cell membrane fraction, and at 100,000 G for 1.5 hours for separation of a cytoplasmic fraction.

The luciferase activity of the magnetic particle, cell membrane and cytoplasm fractions was determined with a Pica Gene luminescence kit (Toyo Ink), and the amounts of their luminescence was determined with a luminometer. Thus, the expression of the luciferase gene introduced was confirmed, and the expression amount determined. The result is shown in Table 1.

TABLE 1

|  | E. coli | Magnetic bacterium |
|---|---|---|
| Cytoplasmic fraction | 0.937 | 42.699 |
| Cell membrane fraction | 0.036 | 37.800 |
| Magnetic fine particle fraction | — | 85.429 |

(Unit: kilo-counts/μg of protein)

As shown in Table 1, the luciferase gene was scarcely expressed in E. coli, while the amount of luminescence from the cytoplasmic fraction was large, which shows that the protein of interest is water-soluble. With the magnetic bacterium, luminescence was observed in all the fractions including cytoplasmic, cell membrane and magnetic fine particle fractions, and luminescence in the magnetic particle fraction was the most intense, which shows that the protein of interest expressed most efficiently on the surface of magnetic fine particles. Namely, it was confirmed that the mps fusion protein or a membrane binding protein, though being water-soluble itself, expressed itself most intensely in the magnetic particle fraction, and that the luc protein on the organic membrane covering magnetic particles was produced and isolated.

Example 2

Figure 5:
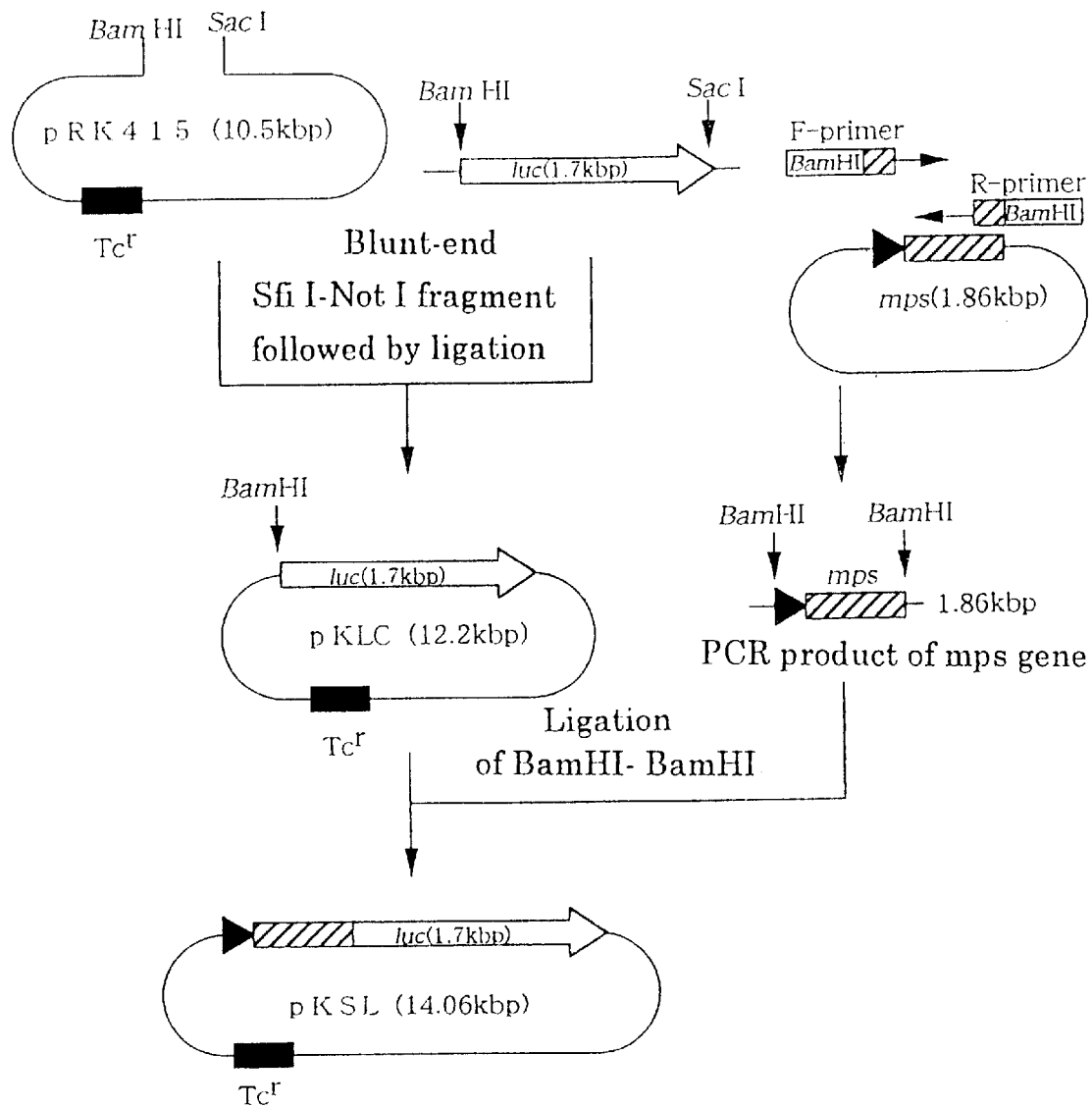
FIG. 5 illustrates the method of preparation of the plasmid pKSG prepared in Example 2.

In order to produce, on an organic membrane mainly composed of phospholipids and covering magnetic particles, an antibody protein encoded by a gene which codes for an antigen recognition site of an anti-rabbit IgG antibody (igg gene, provided by Pharmacia), a plasmid pKSG ligated with an mps-igg fusion gene was prepared by the method as indicated in FIG. 5.

A plasmid pRK415 which can introduce a gene through conjugative transfer into the magnetic bacterium AMB-1 and has a tetracycline resistance gene was used as a vector. pRK415 was cut by Eco RI, and the cut ends were made blunt, to which was attached an igg gene, to produce a plasmid pKGC.

Figure 6:
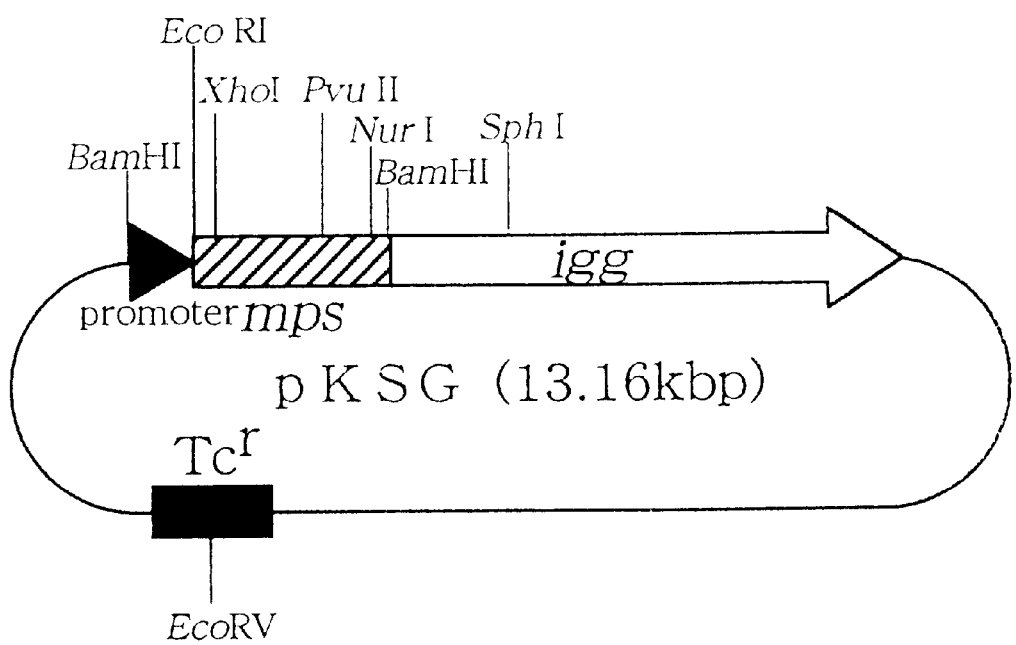
FIG. 6 is a map of restriction enzyme cleavage sites of the plasmid pKLC.

Next, by PCR using an F-primer and R-primer which have respective sequences complementary to a gene fragment comprised of the mps structural gene and a promoter segment present upstream thereof and have been designed for an Bam HI recognition site, amplification was effected, to produce a binding DNA sequence having Bam HI recognition sites at both ends. The thus amplified binding DNA sequence was ligated with the plasmid pKGC to produce a plasmid pKSG. The restriction enzyme cleavage site map of pKSG is shown in FIG. 6. Above procedures allow the igg gene to be translated without causing any shift from the reading frame of the mps, to produce a fusion protein.

This plasmid was introduced through conjugative transfer into a wild strain AMB-1 in the same manner as in Example 1, to produce a transconjugant. The transconjugant was grown on medium, the cells were recovered and disrupted, and magnetic particles were recovered. Immunoassay was performed on the magnetic particles using rabbit IgG as an antigen. Immunoassay was practiced by the sandwich method using an anti-rabbit IgG antibody labeled with alkaline phosphatase as a secondary antibody. Assay was achieved by measuring the luminescence resulting from the reaction between alkaline phosphatase and AMPPD (Boehringer Mannheim Biochemica) with a luminometer. It was found that the antigen can be detected by this method.

Through this experiment it was possible to produce magnetic particles applicable to an antigen detection system without requiring an antibody immobilization operation, by allowing an antibody to bind to magnetic particles of a conjugated cell as an mps fusion protein.

Example 3

Figure 7:
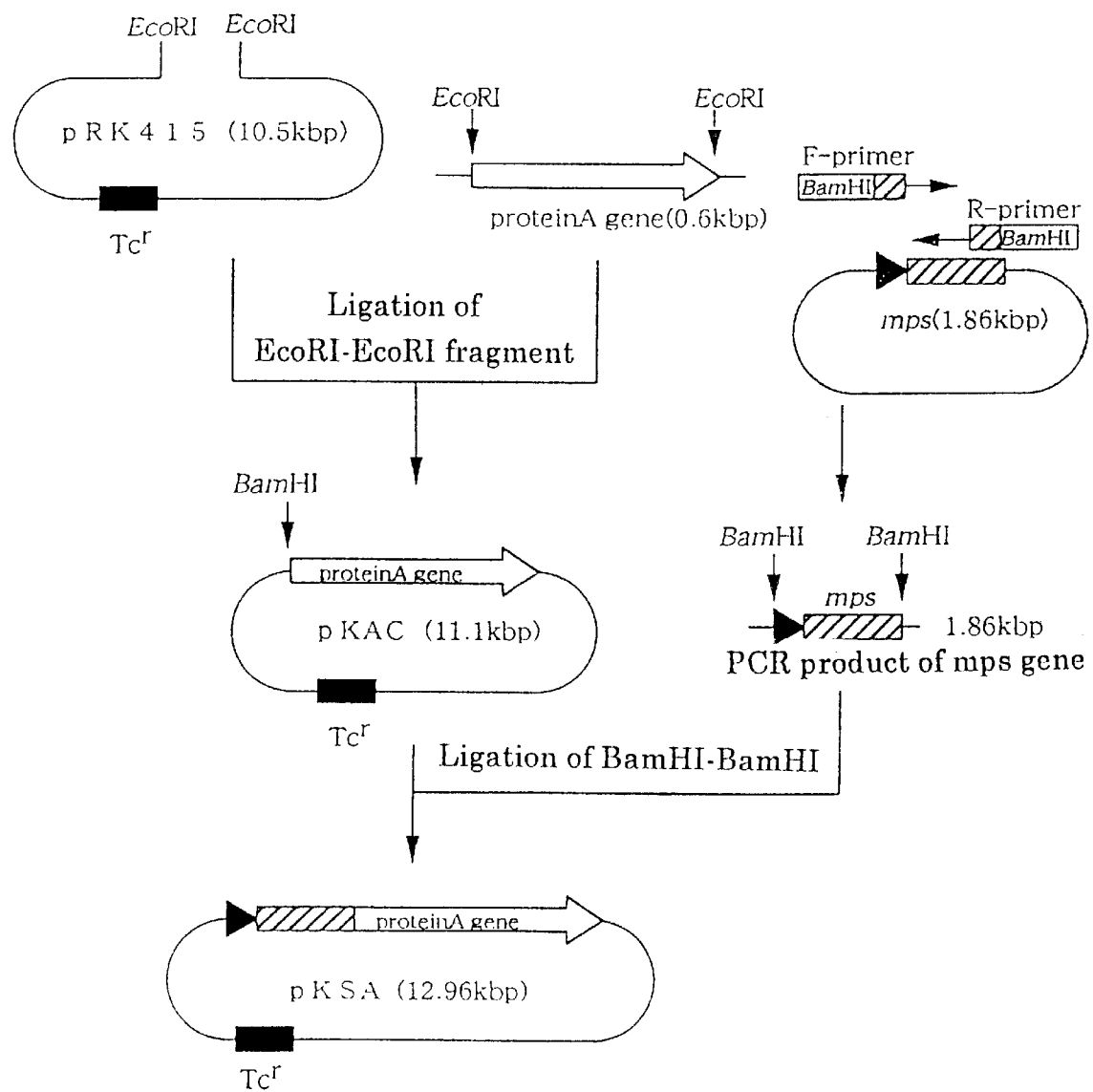
FIG. 7 illustrates the method of preparation of the plasmid pKGA prepared in Example 3.

In order to produce, on an organic membrane mainly composed of phospholipids and covering magnetic particles, a protein encoded by a protein A gene (protein A gene isolated from pEZZ18 provided by Pharmacia), a plasmid pKSA ligated with an mps-protein A fusion gene was prepared by the method as indicated in FIG. 7.

A plasmid pRK415 which can introduce a gene through conjugative transfer into the magnetic bacterium AMB-1, and has a tetracycline resistance gene was used as a vector. pRK415 was cut by Eco RI. In a separate run, a protein A gene added with Eco RI recognition sites was prepared and amplified by PCR using primers designed for Eco RI recognition sites for the both terminals. The protein A gene was incorporated into the pRK415 which had been cut by Eco RI as described above, to produce a plasmid pKAC.

Figure 8:
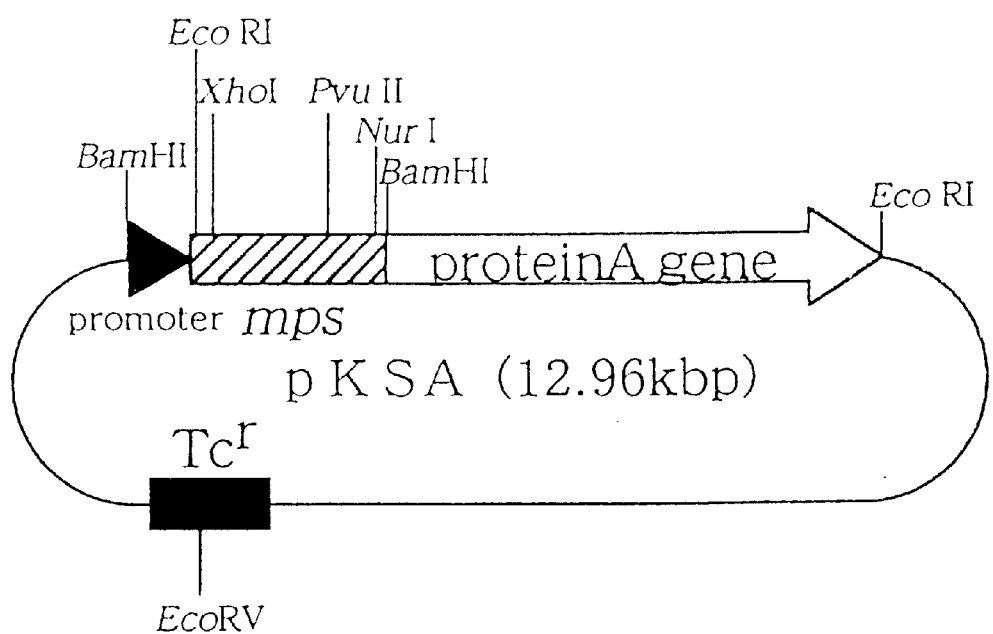
FIG. 8 is a map of restriction enzyme cleavage sites of the plasmid pKSA.

Next, by PCR using an F-primer and R-primer which have respective sequences complementary to a gene fragment comprised of the mps structural gene and a promoter segment present upstream thereof and have been designed for an Bam HI recognition site, amplification was effected, to produce a binding DNA sequence having Bam HI recognition sites at both ends. The thus amplified binding DNA sequence was ligated with the plasmid pKAC to produce a plasmid pKSA. The restriction enzyme cleavage site map of pKSA is shown in FIG. 8. Above procedures allow the protein A gene to be translated without causing any shift from the reading frame of mps. to produce a fusion protein.

This plasmid was introduced through conjugative transfer into a wild strain AMB-1, to produce a transconjugant. Because E. coli S17-1 serving as a host bacterium during conjugative transfer has a tra gene, it can achieve conjugative transfer without requiring a helper plasmid. For conjugative transfer, magnetic bacteria grown on MSGM medium to a middle to late logarithmic phase with a density of about $8 \times 10^7$ cells/ml were used. One day before, the plasmids were introduced into the host bacteria, and developed colonies were scraped off and suspended in a density of $10^9 - 10^{10}$ cells/ml. The two kinds of bacteria were mixed at a ratio of 1:50 (magnetic bacteria: E. coli), and the mixture was spotted on an agar plate to allow mating. Six hours later, the spot was cut out with a scalpel, and bacterial cells were recovered using about 5 ml of MSGM medium. The suspension was inoculated onto an MSGM medium added with 2.5 μg/ml of tetracycline. Incubation was carried out at 25° C. to allow proliferating cells to transform into transconjugantes. In this incubation, E. coli does not grow on this MSGM medium.

Next, magnetic particles were separated from the magnetic bacteria which had been cultured on the MSGM medium after the conjugative transfer. The magnetic bacteria, after being collected by centrifugation, were washed twice with 10 mM Tris buffer, and suspended to give a concentration of not more than 0.1 g wet cell/ml, followed by supersonic disruption treatment, in which supersonic disruption under the conditions of an output of 120 W and a duration of 30 sec was repeated five times. While the cell-disrupted suspension contained in a vessel was cooled with ice, an Sm—Co magnet was applied on the external wall of the vessel for 30 minutes, to separate magnetic particles in the suspension. Thus, magnetic particles on which protein A was expressed were obtained.

With an attention paid to the binding activity of protein A to IgG, the magnetic particles were allowed to mix with anti-cedar pollen, anti-wheat, on anti-egg IgG antibodies. After mixing, the particles were washed, and the immobilized amount of antibodies was measured. As a result if was shown that it is possible with this method to obtain the same amount of immobilized antibodies as that obtained by chemical binding using SPDP as described in Japanese Pre-examination Patent Publication (KOKAI) No. 5-209884, In addition, detection experiments were carried out as in Example 1 of the same publication, resulting in that all the three test antigens were detectable. As seen from above, it was shown that with this method it is possible to easily bind various IgG antibodies to magnetic particles by the use of the protein A-mps fusion protein, and that it is possible to effect antigen detection comparable to conventional chemical binding.

Example 4

Figure 9:
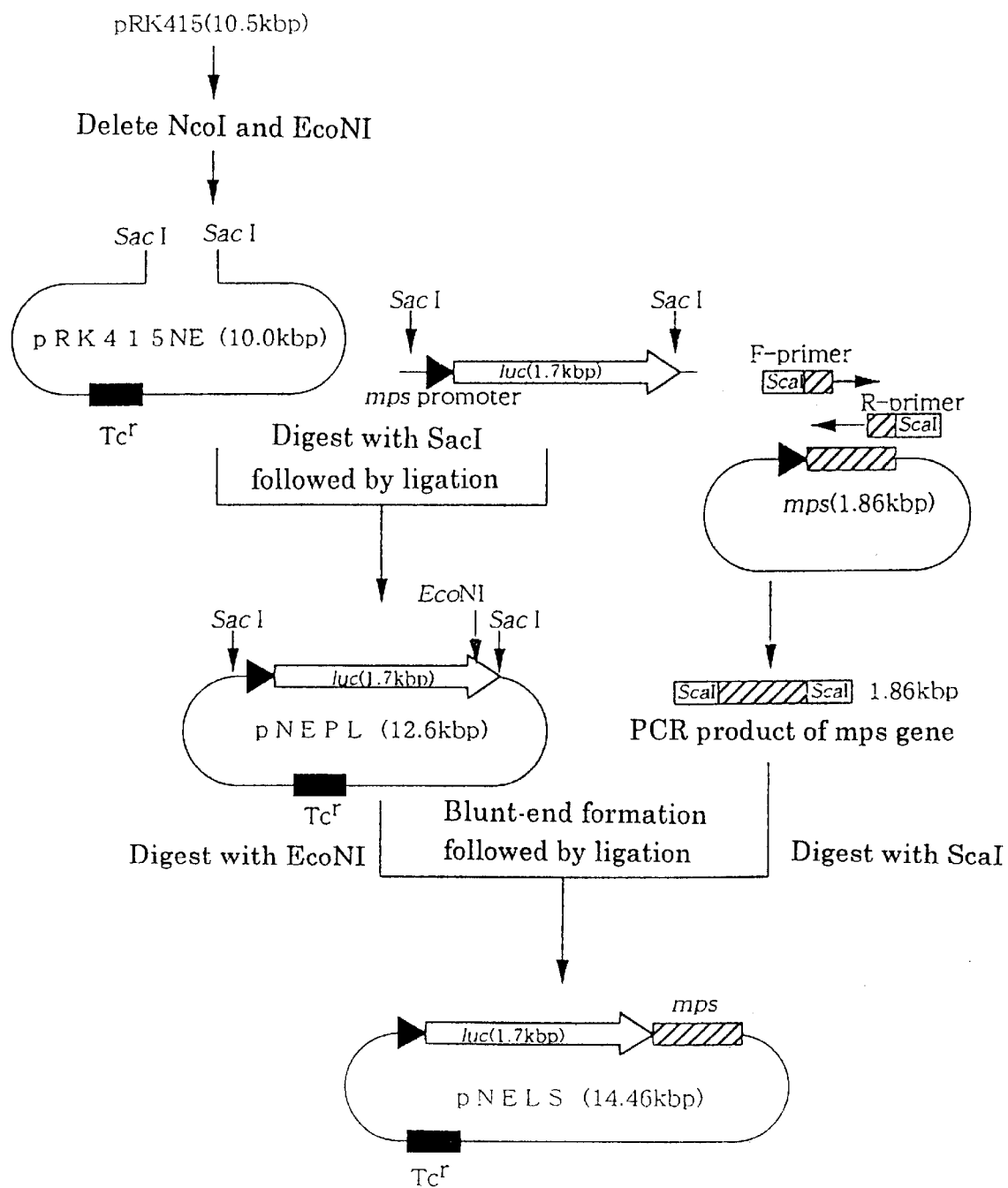
FIG. 9 illustrates the method of preparation of the plasmid pNELS prepared in Example 4.

A firefly luciferase gene (luc gene) was introduced to the 5' terminal of the mps structural gene, and a plasmid pNELS which contains a luc-mps fusion DNA sequence was prepared by the method as shown in FIG. 9.

(1) A plasmid pRK415 which can introduce a gene through conjugative transfer into the magnetic bacterium AMB-1 and has a tetracycline resistance gene was used as a vector. The cut sites of pRK415 by NcoI and EcoNI were made blunt through blunt ending treatment, thereby to produce a plasmid pRK415NE. pRK415NE was cut with SacI, to produce a plasmid pNEPL in which an mps promoter-luc fusion gene has been incorporated.

Figure 10:
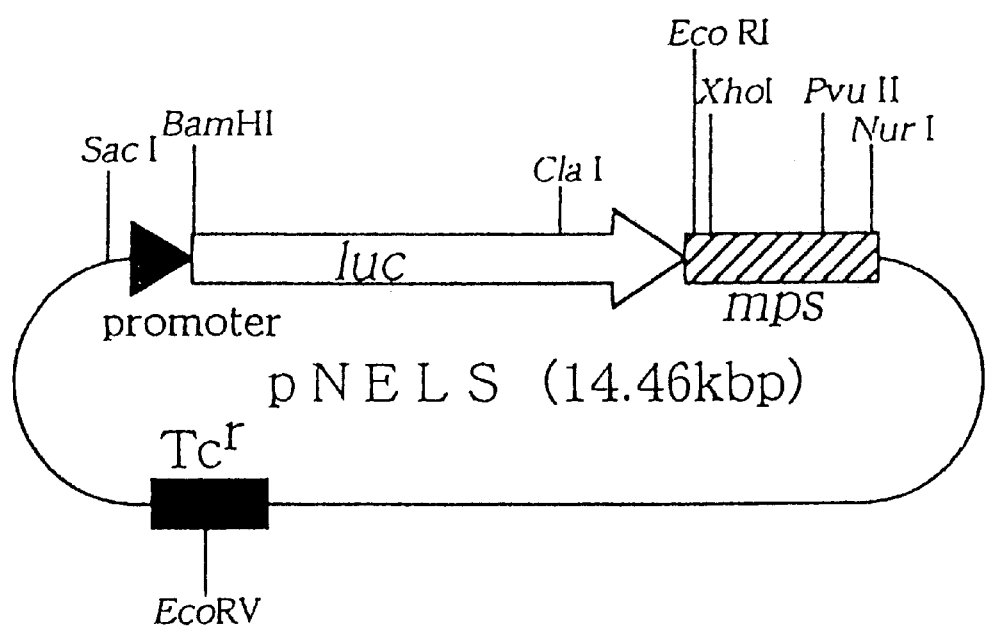
FIG. 10 is a map of restriction enzyme cleavage sites of the plasmids pNELS.

(2) Next, by PCR using primers designed for a ScaI recognition site, an mps gene fragment added with ScaI recognition sites was amplified. The ScaI cleavage sites of the thus amplified mps gene fragment were made to have blunt ends, and ligated with a plasmid pNEPL, which had been digested by EcoNI followed by blunt end formation, to produce a plasmid pNELS. The restriction enzyme cleavage site map of pNELS is shown in FIG. 10.

(3) This plasmid was introduced through conjugative transfer into an wild strain AMB-1 to produce a transconjugant. The transconjugant was cultivated for proliferation, and the cells were recovered and disrupted. Magnetic particles were recovered with a magnet. The luciferase activity of the magnetic particles was determined with a Pica Gene luminescence kit (Toyo Ink), and the amount of luminescence was determined with a luminometer. The result is shown in Table 2.

TABLE 2

|  | pKSL | pNELS |
| --- | --- | --- |
| Magnetic fine particle fraction | 1960 | 366.4 |

(Unit: kilo-counts/µg of protein)

Next, in order to check in which direction C- and N-terminals of the mps protein on magnetic particles are exposed, magnetic particles produced in a transconjugant which holds a plasmid pKSL with a luc gene bound to 3' terminal of the mps structural gene, and magnetic particles produced in the transconjugant which holds a plasmid pNELS with a luc gene bound to 5' terminal of the mps structural gene were subject to immunoassay using anti-luciferase IgG and alkaline phosphatase-labeled anti-rabbit IgG. Assay was achieved by measuring the luminescence resulting from the reaction between alkaline phosphatase and AMPPD (Boehringer Mannheim Biochemica) with a luminometer. The result is shown in Table 3.

TABLE 3

|  | AMB-1 | pKSL | pNELS |
| --- | --- | --- | --- |
| Magnetic fine particle fraction | 37 | 2320 | 1560 |

(Unit: kilo-counts/mg of protein)

From this experiment it was demonstrated that N- and C-terminals of mps protein are exposed to space outside the organic membrane covering magnetic particles. Accordingly, selection can be made depending on the nature of the functional protein as to whether a functional protein is to be expressed as a fusion protein fused with N-terminal of mps protein, or as a fusion protein fused with C-terminal of mps protein.

Example 5

Figure 11:
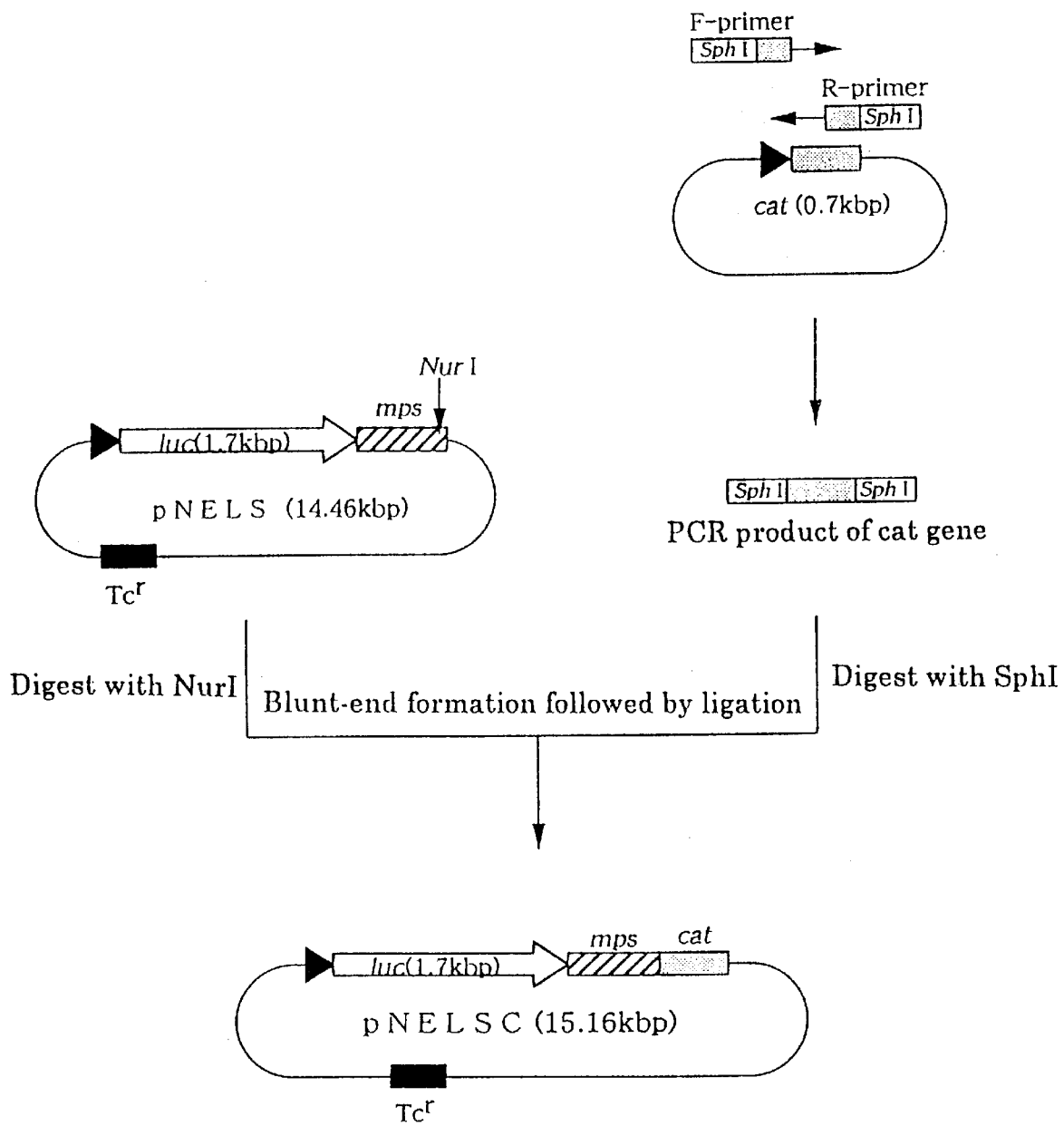
FIG. 11 illustrates the method of preparation of the plasmid pNELSC prepared in Example 5.

In order to allow a firefly luciferase gene and chloramphenicol acetyl transferase (CAT) gene to express simultaneously on magnetic particles, a plasmid pNELSC containing a luc-mps-cat fusion DNA sequence was prepared by the method as indicated in FIG. 11.

Figure 12:
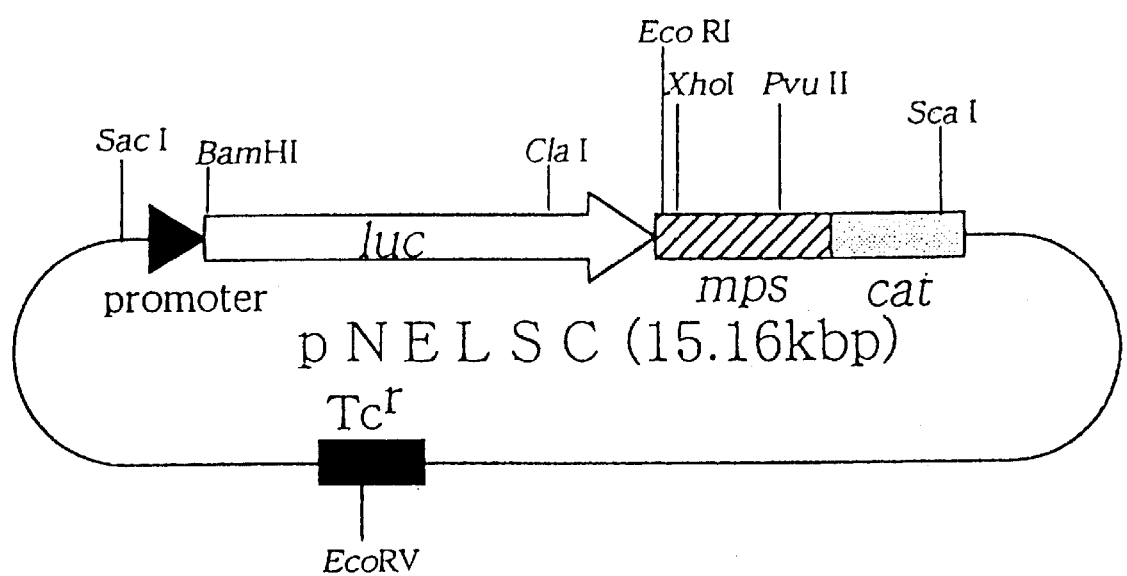
FIG. 12 is a map of restriction enzyme cleavage sites of the plasmid pNELSC.

Primers prepared by deleting the SD sequence from CAT gene and designed for SphI recognition sites were used. PCR based on the use of the primers was applied to a cat gene fragment, so that a cat gene fragment added with SphI recognition sites was amplified. The SphI cleavage sites of the thus amplified cat gene fragment were made to have blunt ends. This was ligated with a fragment prepared by digesting pNELS prepared in Example 4 with NurI followed by blunt end formation, to produce a plasmid pNELSC. The restriction enzyme cleavage site map of pNELSC is shown in FIG. 12. This plasmid was introduced through conjugative transfer into a wild strain AMB-1 to produce a transconjugant. The conjugated cells were cultivated to proliferate, and the cells were recovered and disrupted. Magnetic particles were recovered with a magnet. The luciferase activity of the magnetic particles was determined with a Pica Gene luminescence kit (Toyo Ink), and their luminescence was assayed with a luminometer. It was found that the luciferase activity was equivalent in intensity to that from pNELM.

Next, CAT on the magnetic particles was assayed, and it was found to have an activity. The CAT assay was conducted by detecting acetylated chloramphenicol to be produced by the reaction of chloramphenicol acetyl transferase and chloramphenicol according to thin-layer chromatography. As a result it was found that each of proteins bound to different ends of the mps structural gene protein has an activity equivalent to that exhibited when the protein is bound singly. Through this experiment it became possible to construct a fusion gene by binding genes coding for functionally different proteins to both ends of the mps structural gene, thereby enabling simultaneous expression of the proteins on magnetic particles and production of magnetic particles with multiple functions.

Example 6

I. Preparation of recombinant plasmid

Figure 13:
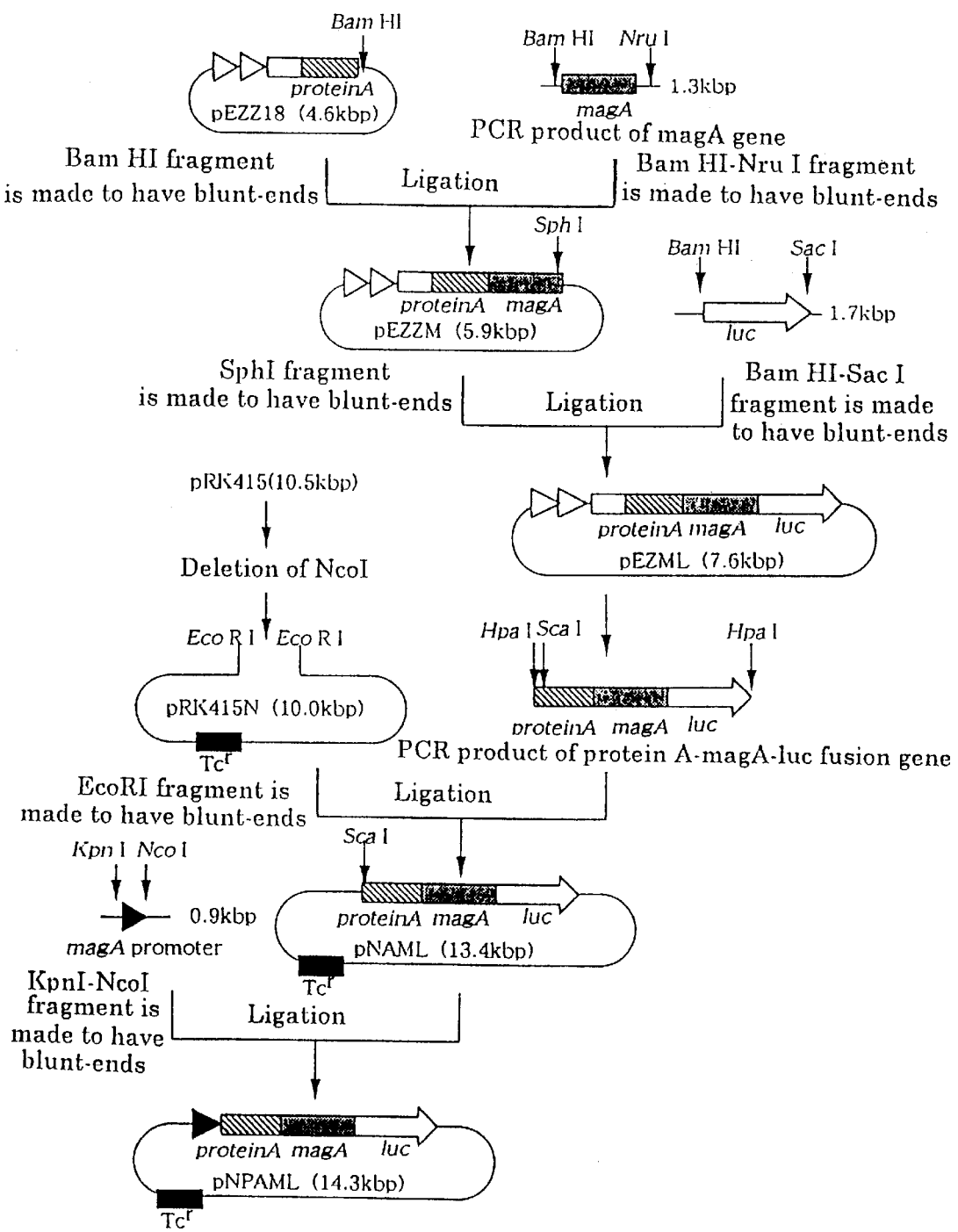
FIG. 13 illustrates the method of preparation of the plasmid pNPAML prepared in Example 6.

A firefly luciferase gene (luc gene, produced by Toyo Ink) was ligated with 3' terminal of the mag A gene, and protein A gene (protein A gene produced by Pharmacia) was ligated with 5' terminal of the same mag A gene. A plasmid pNPAML containing the resulting protein A-mag A-luc fusion DNA sequence was prepared by the method as shown in FIG. 13.

A plasmid pRK415 (N. T. Neen, S. Tamaki, D. Kobayashi and D. Trallinger, 1988, Gene 70:191–197) which can introduce a gene through conjugative transfer into the magnetic bacterium AMB-1, and has a tetracycline resistance gene was used as a final vector.

(1) By PCR using primers designed for BamHI and NurI recognition sites, an mag A gene fragment added with BamHI and NurI recognition sites was amplified, followed by blunt end formation. The blunt-end mag A gene fragment, after being digested with BamHI, was introduced into a plasmid pEZZ18 which had been made to have blunt ends, to produce a plasmid pEZZM.

(2) Next, a luc gene, after having been digested with BamHI and SacI and made to have blunt ends, was digested with SpnI and introduced into the plasmid pEZZM whose ends had been mad blunt, to produce a plasmid pEZML which contains a protein A-mag A-luc fusion DNA sequence. Further, by PCR using primers designed for HpaI and ScaI recognition sites, a protein A-mag A-luc fusion DNA sequence added with HpaI and ScaI recognition sites was amplified.

(3) Next, into a plasmid pRK415 from which the NcoI recognition site had been deleted was digested with EcoRI, followed by blunt end formation, the protein A-mag A-luc fusion DNA sequence amplified by PCR was incorporated, to produce a plasmid pNAML.

(4) Next, the plasmid pNAML was digested with ScaI, while a plasmid pUM5 was digested with KpnI and NcoI. Then, a promoter sequence of a mag A gene which had been treated to have blunt ends was incorporated. Thus, a plasmid pNPAML which contains the promoter of mag A gene, and the protein A-mag A-luc fusion DNA sequence was prepared.

II. Preparation of transconjugant

Next, the plasmid obtained by Section I was introduced through conjugative transfer into an wild strain AMB-1 to produce a transconjugant. Because *E. coli* S17-1 serving as a host bacterium during conjugative transfer has a tra gene, it can achieve conjugative transfer without a helper plasmid. For conjugative transfer, magnetic bacteria grown on MSGM medium to a middle to late logarithmic phase with a density of about $8\times10^4$ cells/ml were used. One day before, the plasmids were introduced into the host bacteria, and developed colonies were scraped off and suspended to give a density of $10^9$–$10^{10}$ cells/ml. The two kinds of bacteria were mixed at a ratio of 1:50 (magnetic bacteria *E. coli*), and the mixture was spotted on an agar plate to allow mating. Six hours later, the spot was cut out with a scalpel, and bacterial cells were recovered using about 5 ml of MSGM medium. The suspension was inoculated onto an MSGM medium added with 2.5 µg/ml of tetracycline. The culture was incubated at 25° C. to allow proliferating cells to transform into transconjugantes. In this cultivation, *E. coli* does not grow on this MSGM medium.

Next, magnetic particles were separated from the magnetic bacteria which had been cultured on the MSGM medium after the conjugative transfer. The magnetic bacteria, after being collected by centrifugation, were washed twice with 10 mM Tris buffer, and suspended to give a concentration of not more than 0.1 g wet cell/ml. Then, the *coli* suspension was submitted to a supersonic disruption treatment in which disruption at an output of 120 W for 30 sec was repeated five times. While the cell-disrupted suspension contained in a vessel was cooled with ice, an Sm—Co magnet was applied on the external wall of the vessel for 30 minutes, to separate magnetic particles in the suspension. Thus, magnetic particles upon which firefly luciferase and protein A expressed themselves simultaneously were obtained.

Next, the isolated magnetic particles were suspended in a phosphate buffered saline (PBS, pH 7.4), to which was added anti-human IgG antibodies, to allow them to bind to protein A. Excess antibodies were washed off by repeating the operation of recovering the magnetic particles magnetically with a Sm—Co magnet and then suspending them in a PBS again. Thus magnetic particles upon which the antibodies were bound to protein A were obtained.

Next, to a suspension of the magnetic particles upon which firefly luciferase and protein A were expressed simultaneously, the magnetic particles having the anti-human IgG antibodies bound thereto, (protein A expressed and antibody bound magnetic particle) was added human IgG as an antigen, to allow an antigen-antibody reaction to occur. The antigen-antibody reaction was allowed to occur while the suspension was stirred through the application of an alternating magnetic field (Japanese Pre-examination Patent Publication (KOKAI) No. 2-281142). Magnetic particles on which protein A and luciferase had been immobilized by conventionally used chemical binding method using glutaraldehyde (Japanese Pre-examination Patent Publication (KOKAI) No. 6-12994), and anti-human IgG antibody was bound to the protein A (protein A immobilized and antibody bound magnetic particle), and magnetic particles on which anti-human IgG antibody luciferase had been immobilized (antibody bound magnetic particle)were used for comparison. Aggregation resulting from the antigen antibody reaction changed the amount of luminescence due to luciferase on the magnetic particles, the change in the luminescence was followed, and the results are shown in Table 1. The luciferase activity was determined with a Pica Gene luminescence kit (Toyo Ink), and the luminescence was assayed with a luminometer. The maximum detection sensitivity was compared by measurement being conducted for diluted antigens.

TABLE 4

|   | Maximum detection sensitivity (ng/ml) |
|---|---|
| Protein A expressed and antibody bound magnetic particle | 0.025 |
| Protein A immobilized and antibody bound magnetic particle | 0.1 |
| Antibody immobilized magnetic particle | 5.0 |

As shown in Table 4, the protein A expressed and antibody bound magnetic particle has the highest detection sensitivity. This is because, in contrast with chemical immobilization, with this method where a protein is allowed to express itself through gene recombination, binding sites on magnetic particle are genetically controlled, and thus the enzyme activity suffers no impairment. As it is also possible to put protein A and luciferase close to each other through genetic control, luminescence from luciferase can be effectively suppressed due to antigen binding. By contrast, with chemical immobilization, active sites may be consumed for immobilization, or steric hindrance may arise depending on the state of the bound protein, which may interfere with the exposure of the binding site to the surface. Accordingly, it is difficult to control the amount of immobilization, or to stably immobilize two kinds of protein simultaneously.

Example 7

I. Preparation of recombinant plasmid

Figure 14:
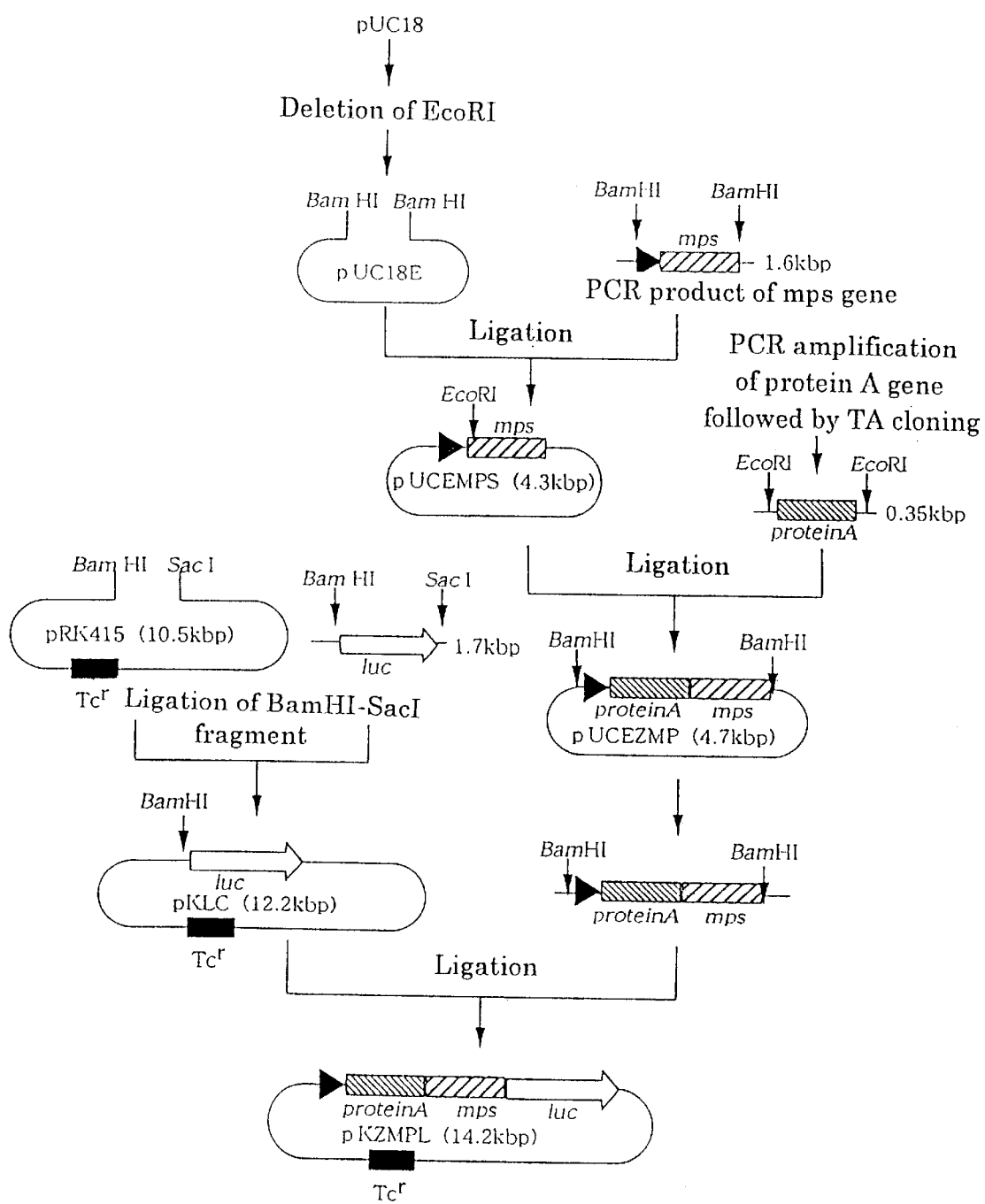
FIG. 14 illustrates the method of preparation of the plasmid pKZMPL prepared in Example 7.

A plasmid pKZMPL in which a firefly luciferase gene (luc gene, produced by Toyo Ink) was ligated with 3' terminal or a mps gene, and a protein A gene (protein A gene produced by Pharmacia) was ligated with 5' terminal of the same mps gene and which thus contains a protein A-mps-luc fusion DNA sequence, was prepared by the method as shown in FIG. 14.

A plasmid pRK415 (N. T. Neen, S. Tamaki, D. Kobayashi and D. Trallinger, 1988 Gene 70:191–197) which can introduce a gene through conjugative transfer into the magnetic bacterium AMB-1, and has a tetracycline resistance gene, was used as a final vector.

(1) EcoRI recognition site was deprived from a plasmid pUC18 to prepare pUC18E. By PCR using primers designed for BamHI recognition sites, a mps gene segment containing a promoter sequence and BamHI recognition sites were amplified. The resulting mps gene fragment was ligated with a plasmid the UC18E which had been digested at BamHI recognition sites, to produce a plasmid pUCEMPS.

(2) Next, the protein A gene, having been amplified by PCR, was extracted through digestion by EcoRI from plasmids having undergone TA cloning. The extracted protein A gene fragment was ligated with the plasmid UCEMPS which had been digested with EcoRI, to produce a plasmid pUCEZMP.

(3) Next, a plasmid pRK415 wad digested with BamHI and SacI, and into the resulting plasmid was incorporated a luc gene which had been digested with BamHI and SacI, to produce a plasmid pKLC. Further, the plasmid pKLC was cut at a BamHI recognition site upstream of the luc gene.

(4) The plasmid pUCEZMP was digested with BamHI, to extract a protein A mps fusion DNA sequence, which was then ligated with the plasmid pKLC which had been digested with BamHI, to produce a plasmid pKZMPL containing a protein A-mps-luc fusion DNA sequence.

II. Preparation of transconjugant

Next, the recombinant plasmid obtained by Section I was introduced through conjugative transfer into an wild strain AMB-1 to produce a transconjugant. Because *E. coli* S17-1 serving as a host bacterium during conjugative transfer has a tra gene, it can achieve conjugative transfer without requiring a helper plasmid. For conjugative transfer, magnetic bacteria grown on MSGM medium to a middle to late logarithmic phase with a density of about $8 \times 10^7$ cells/ml were used. One day before, the plasmids were introduced into the best bacteria, and developed colonies were scraped off and suspended to give a density of $10^9$–$10^{10}$ cells/ml. The two kinds of bacteria were mixed at a ratio of 1:50 (magnetic bacteria:*E. coli*), and the mixture was spotted on an agar plate to allow mating. Six hours later, the spot was cut out with a scalpel, and bacterial cells were recovered using about 5 ml of MSGM medium. The suspension was inoculated onto an MSGM medium added with 2.5 µg/ml of tetracycline. The culture was incubated at 25° C. to allow proliferating cells to transform into transconjugants. In this cultivation, *E. coli* does not grow on this MSGM medium.

Next, magnetic particles were separated from the magnetic bacteria which had been cultured on the MSGM medium after the conjugative transfer. The magnetic bacteria, after being collected by centrifugation, were washed twice with 10 mM Tris buffer, and suspended to give a concentration of not more than 0.1 g wet cell/ml. Then, the cell suspension was submitted to a supersonic disruption treatment in which disruption under an output of 120 W for 30 sec was repeated five times. While the cell-disrupted suspension contained in a vessel was cooled with ice, an Sm—Co magnet was applied on the external wall of the vessel for 30 minutes, to separate magnetic particles in the suspension. Thus, magnetic particles upon which firefly luciferase and protein A expressed simultaneously were obtained.

Next, the isolated magnetic particles were suspended in a phosphate buffered saline (PBS, pH 7.4), to which was added anti-human IgG antibodies, to allow them to bind to protein A. Excess antibodies were washed off by repeating the operation of recovering the magnetic particles magnetically with a Sm—Co magnet and then suspending them in a PBS again. Thus magnetic particles upon which the antibodies were bound to protein A were obtained.

Next, to a suspension of the magnetic particles upon which firefly luciferase and protein A were expressed simultaneously, the magnetic particles having the anti-human IgG antibodies bound thereto, (protein A expressed and antibody bound magnetic particle) was added human IgG as an antigen, to allow an antigen-antibody reaction to occur. The antigen-antibody reaction was allowed to occur while the suspension was stirred through the application of an alternating magnetic field (Japanese Pre-examination Patent Publication (KOKAI) No. 2-281142). Magnetic particles on which protein A and luciferase had been immobilized by conventionally used chemical binding method using glutaraldehyde (Japanese Pre-examination Patent Publication (KOKAI) No. 6-12994), and anti-human IgG antibody was bound to the protein A (protein A immobilized and antibody bound magnetic particle), and magnetic particles on which anti-human IgG antibody luciferase had been immobilized (antibody bound magnetic particle) were used for comparison. Aggregation resulting from the antigen-antibody reaction changed the amount of luminescence due to luciferase on the magnetic particles, the change in the luminescence was followed, and the results are shown in Table 1. The luciferase activity was determined with a Pica Gene luminescence kit (Toyo Ink), and the luminescence was assayed with a luminometer. The maximum detection sensitivity was compared by measurement being conducted for diluted antigens.

TABLE 5

|  | Maximum detection sensitivity (ng/ml) |
| --- | --- |
| Protein A expressed and antibody bound magnetic particle | 0.010 |
| Protein A immobilized and antibody bound magnetic particle | 0.1 |
| Antibody immobilized magnetic particle | 5.0 |

As shown in Table 5, the protein A expressed and antibody bound magnetic particle has the highest detection sensitivity. This is because, in contrast with chemical immobilization, with this method where a protein is allowed to express itself through gene recombination, binding sits on magnetic particle are genetically controlled, and thus the enzyme activity suffers little impairment. As it is also possible to put protein A and luciferase close to each other by controlling genetically, luminescence from luciferase due to antigen binding can be effectively suppressed. By contrast, with chemical immobilization, active sites may be consumed for immobilization, or steric hindrance may arise depending on the state of the bound protein, which may interfere with the exposure of binding sites to the surface. Accordingly, it is difficult to control the amount of immobilized proteins, or to stably immobilize two kinds of protein simultaneously.

Advantages of the invention

This invention dispenses with an immobilization treatment, and ensures stable production of a useful protein such as antibody or the like bound to an organic membrane of magnetic particles by only cultivating a transformed magnetic bacterium, and separating magnetic particles generated in the interior of the bacterium. When a useful protein is a functional protein, it is possible to move it to a desired location so that it can effectively develop its function there, because the functional protein immobilized on a magnetic particle can be controlled magnetically.

Further, this invention allows any protein to be produced on a magnetic particle, by introducing a gene coding for a desired protein into a plasmid vector, and by transforming a magnetic bacterium with the thus obtained recombinant plasmid.

This invention does not require providing of a protein such as expensive enzymes, antibodies, etc., enables semi-permanent production of magnetic particles to which a desired protein is bound by only maintaining and cultivating the same bacterial strain, gives little variation among production lots with respect to the content and activity of a protein product, and is greatly beneficial due to its low cost. In addition, the magnetic particle thus produced always contains the same amount of protein having the same activity.

Furthermore, as this invention allows a desired protein to be produced on a magnetic particle, it is possible to separate and recover the protein in a short period of time, thus enabling an efficient separation/purification of the protein.

According to the method of this invention for assaying a target substance, it is possible to accelerate the reaction between a minute amount of target substance and a binding protein on a magnetic particle, for example, by an alternating magnetic field, thereby to aggregate magnetic particles, and to measure the change in intensity of fluorescence or light emitted by a second protein, thereby enabling a ready assay of the target substance. Further, the magnetic particle to be used in this invention does not require an immobilization treatment, and a functional protein is bound to a magnetic particle exclusively through a biological bond. Thus, no reduction of activity in association with an immobilization treatment will ensue. Furthermore, the immobilization process proceeds evenly due to homogenous reactivity, and requires only a low cost. Still further, as this method allows genetic control of the position where the protein expresses itself, it is possible to bind a binding protein and a labeling protein to positions close to each other, which will contribute to the increased sensitivity for detection. Accordingly, if, for example, a protein A is allowed to express itself to act as a medium, and an antibody is bound thereto to be used for antigen-antibody reaction, light emission from luciferase can be readily suppressed because of the proximity of the antibody bound to an antigen, which ensures a highly sensitive assay.

INDUSTRIAL APPLICAPABILITY

This invention, for example, has following possible applications.

1) Enzyme bound carrier

Any enzyme of which it has been thought ideal to allow them to exercise site-specific actions are worth of being bound to magnetic particle for expression. For example, when it is desirable to allow an enzyme reaction to take place at a certain location in a reaction system during development of a biochemical reaction, a magnetic particle upon which that enzyme can express itself will be valuable. When, in a certain disease with which an enzyme is involved, it is desirable to apply the enzyme specifically to a certain location, it is possible to magnetically guide the enzyme which has been made to express itself on a magnetic particle, to the desired location for therapy.

2) DNA carrier

When a gene coding for a protein capable of binding to DNA or RNA, for example, a protein such as repressor is fused with a binding DNA sequence, and bound to a magnetic particle according to this invention, it is possible to use the magnetic particle as a carrier to deliver the gene. A certain protein such as repressor may loco the binding activity in the presence of a certain other particular substance. It is possible to carry a gene by exploiting such property. Lac I may be cited as such an example of repressor. Lac I is a protein controlling the expression of a gene of a lactose decomposing enzyme, and is a repressor which inhibits the transcription of that gene by binding to a site downstream of the promoter. The Lac I loses the ability to bind to DNA by binding to a chemical substance such as lactose or IPTG. Namely, as long as there is a substrate it can decompose, it expresses its function. Furthermore, there is a particular DNA domain to which Lac I binds. Therefore, to a gene incorporating that DNA domain Lac I can bind.

For example, when this Lac I gene is allowed to express itself on a magnetic particle, it is possible for Lac I to bind to a gene incorporating the DNA domain. On the other hand, Lac I loses its binding activity to DNA in the presence of a substance called IPTG. Thus it is possible to carry DNA magnetically from a certain specific place and to release it by adding IPTG. Through this maneuver it is possible to carry a gene to a desired place.

From above it is reasonable to think that the magnetic particle of this invention be applied as a carrier of a gene in gene therapy. For example, currently a therapy which consists of preparing an anti-sense RNA derived from a strand complementary to a gene of interest, and of suppressing the expression of the gene in question through the formation of the RNA hybrid has been studied widely, and the magnetic particle of this invention can be utilized as a carrier of DNA which is responsible for the expression of the anti-sense RNA.

Furthermore, a protein having a binding activity to a metal is allowed to express itself on a magnetic particle, and this can be utilized for recovery or detection of that metal. The recovery and detection can take place through magnetism.

3) Protein production system

Although it has been said that isolation and purification of a protein is generally difficult, isolation and purification of a protein will become easy by allowing it to express itself on a magnetic particle as a fusion protein fused with mps protein. This is because the protein which is allowed to express itself on a magnetic particle can be readily recovered by a magnetic means at some final stage. Considering that magnetic particles derived from a magnetic bacterium has a high dispersibility, probably there will be many proteins which, even though bound to magnetic particles, are still usable. For example, the enzyme used for alcoholic fermentation is probably sufficiently usable even if it is bound to a magnetic particle, as long as it maintains the enzymatic activity.

4) Diagnostic agents

A magnetic particle can be prepared where a reporter gene of luciferase or the like and an antibody are allowed to express at the same time, or where protein A is allowed to express so as to have an ability to bind to an antibody. Such magnetic particle can be used as a reagent for the assay of immunity. The magnetic particle acts as a carrier, and thus when a magnetic field is applied externally, the solution inclusive thereof can be stirred to facilitate the antigen-antibody reaction. Aggregation as a result of antigen-antibody reaction stereochemically interferes with the expression of the reporter gene, or interferes with light emission when luciferase is the expression result of the gene. As suppression of the light emission varies according to the degree of aggregation, it is possible to quantify the antigen.

5) Quantification of a target substance such as antigenic substances

The aforementioned method consists of incorporating a binding protein and a labeling protein as useful proteins, binding those proteins to a magnetic particle and using the complex for various purposes. According to this method, a protein with a light emitting capacity such as luciferase (luminescence reaction-related enzyme) is bound to a magnetic particle, and an antibody is bound to the same particle for simultaneous expression, or protein A is bound to the same particle, to give an antibody binding activity. The resulting magnetic particle can be used as a reagent for the assay of immunity. The magnetic particle acts as a carrier, and thus when a magnetic field is applied externally, the solution inclusive thereof can be stirred to facilitate the antigen-antibody reaction. Aggregation as a result of antigen-antibody reaction stereochemically interferes with the expression of the functional protein with a light emitting capacity, or interferes with light emission when luciferase is the functional protein. As suppression of the light emission varies according to the degree of aggregation, it is possible to quantify the antigen.

The base sequences listed below in Sequence Listing are arranged left to right from 5' terminal to 3' terminal. Each letter stands for a base as follows.

A: Adenine
G: Guanine
C: Cytosine
T: Thymine
Y: T/U or C
H: A or C
N: A or G or C or T/U
R: G or A

We claim:

1. A protein-bound magnetic particle which comprises:
a magnetic particle which is produced in the cell of a magnetic bacterium, and a hybrid protein bound to an organic membrane covering the magnetic particle; said hybrid protein comprising a polypeptide chain containing at least a membrane-bound portion of a membrane protein which is originally produced in a state of being bound to the organic membrane and at least one other protein which is biologically bound by fusion, antigen-antibody reaction or ligand-receptor reaction to said polypeptide wherein the membrane protein is the mps protein having an amino acid sequence as depicted by SEQ ID NO: 1.

2. The protein bound magnetic particle according to claim 1 wherein the magnetic bacterium is a microorganism of genus Magnetospirillum or Desulfovibrio.

3. The useful protein-bound magnetic particle according to claim 1 wherein the magnetic bacterium is AMB-1.

4. The protein-bound magnetic particle according to claim 1 wherein the at least one other protein has a physiological activity.

5. The magnetic particle according to claim 4 wherein the protein having a physiological activity is an immunity-related protein, a protein having a binding activity, or an enzyme.

6. A protein-bound magnetic particle which comprises:
a magnetic particle which is produced in the cell of a magnetic bacterium, and a hybrid protein bound to an organic membrane covering the magnetic particle; said hybrid protein comprising a polypeptide chain containing at least a membrane-bound portion of a membrane protein which is originally produced in a state of being bound to the organic membrane and at least one other protein which is biologically bound by fusion, antigen-antibody reaction or ligand-receptor reaction to said polypeptide wherein the hybrid protein includes a binding protein and a labeling protein, and these proteins are bound to the polypeptide chain in a state of being close to each other.

7. The magnetic particle according to claim 6 wherein the membrane bound portion contained in the polypeptide chain is derived from the mps protein which has an amino acid sequence as depicted by SEQ ID NO: 1.

8. The magnetic particle according to claim 6 wherein the membrane bound portion contained in the polypeptide chain is derived from the mag A protein which has an amino acid sequence as depicted by SEQ ID NO: 4.

9. A method for producing a protein-bound magnetic particle which comprises:
a magnetic particle which is produced in the cell of a magnetic bacterium, and a hybrid protein bound to an organic membrane covering the magnetic particle; said hybrid protein comprising a polypeptide chain containing at least a membrane-bound portion of a membrane protein which is originally produced in a state of being bound to the organic membrane and at least one other protein which is biologically bound by fusion, antigen-antibody reaction or ligand-receptor reaction to said polypeptide, said method comprising cultivating a magnetic bacterium transformed with a plasmid which contains a fusion DNA sequence resulting from the fusion of a gene fragment coding at least for a membrane-bound portion of a membrane protein which is originally produced in a state of being bound to the organic membrane, and a DNA sequence coding for said at least one other protein, to thereby make said fusion DNA sequence express; thus producing a fusion protein containing said at least one other protein in a state of being bound to the organic membrane covering the magnetic particle in the cell of said bacterium, the fusion DNA sequence comprising:

(a) a gene fragment containing a DNA sequence which codes, out of the amino acid sequence of the mps protein which is produced in a state of being bound to the organic membrane covering the magnetic particle produced in the cell of the magnetic bacterium AMB-1, for the portion bound to the organic membrane; and (b) one or more DNA sequences which respectively code for one or more proteins which are fused with one or both ends of said gene fragment.

10. A recombinant plasmid containing a fusion DNA sequence which comprises:

(a) a gene fragment containing a DNA sequence which codes, out of the amino acid sequence of the mps protein which is produced in a state of being bound to the organic membrane covering the magnetic particle produced in the cell of the magnetic bacterium AMB-1, for the portion bound to the organic membrane; and (b) one or more DNA sequences which respectively code for one or more proteins which are fused with one or both ends of said gene fragment.

11. A transformed magnetic bacterium comprising a host magnetic bacterium and a recombinant plasmid according to claim 10 introduced into said host magnetic bacterium.

12. The transformed magnetic bacterium according to claim 11, wherein said host magnetic bacterium is a microorganism belonging to the genus Magnetospirillum or to the genus Desulfovibrio.

13. A method for assaying a target substance in a sample which comprises:

(A) adding magnetic particle to which is bound a binding protein which binds specifically to the target substance and to which is bound a labeling protein, to the sample, so that, if the target substance is present at all in the sample, it reacts with that binding protein to cause magnetic particles to aggregate;

(B) next, measuring signals based on the presence of the labeling protein after aggregation; and (C) comparing the intensity of the thus obtained signals with those from a standard sample, to quantify the target substance in the sample, wherein the binding protein and labeling protein are bound close to each other through fusion, antigen-antibody reactions or ligand-receptor reactions to a polypeptide chain which contains at least a membrane-bound portion of a membrane protein produced in a state of being bound to an organic membrane covering the magnetic particle which is produced in the cell of a magnetic bacterium.

14. The method according to claim 13 wherein the binding protein is bound to one end of the polypeptide chain, and the labeling protein is bound to the other end of the same polypeptide chain.

15. The method according to claim 13, wherein at least one of the binding and labeling proteins is bound through fusion to the membrane protein.

16. The method according to claim 13, wherein the binding protein or the labeling protein is fused with one end of the polypeptide chain, and the remaining labeling protein or the binding protein is further fused in series with the thus fused protein.

17. The method according to claim 13, wherein at least one of the binding and labeling proteins is bound biologically by fusion, antigen-antibody reaction or ligand-receptor reaction to another protein that has been bound through fusion to the membrane protein.

18. The method according to claim 13, wherein said protein produced in a state of being bound to the organic membrane is bound to the organic membrane through the membrane-bound portion of mag A protein or mps protein.

19. The method according to claim 13, wherein protein A is fused with one end of the polypeptide chain containing at least a membrane-bound portion of the membrane protein, an anti-IgG antibody or a binding protein is bound to the protein A, and a labeling protein is fused with the other end of the polypeptide chain.

20. The method according to claim 13, wherein the target substance is selected from an antigen, an antibody, substances which can bind as ligand to a protein, polysaccharides/complex carbohydrates, and biotin, and the binding protein is selected from proteins which act as an antibody or antigen in correspondence with said target substance, proteins which bind to said ligand, protein A, lectins and avidins.

21. The method according to claim 13, wherein the labeling protein is a fluorescent protein, a fluorescent dye-binding protein, or an enzyme.

22. The method according to claim 21, wherein the enzyme is a luminescence-related enzyme, coenzyme, hydrolase, oxidation-reduction enzyme, catalase, transferase, elimination enzyme, or restriction enzyme.

23. The method according to claim 21 wherein the enzyme is luciferase, alkaline phosphatase, peroxidase, β-D-galactocidase, glucose oxidase, or glucose-6 phosphate dehydrogenase.

24. Isolated and purified mps protein which is produced in a state of being bound to an organic membrane covering a magnetic particle produced in the cell of the magnetic bacterium AMB-1, and consists of the amino acid sequence as indicated by SEQ ID NO: 1.

25. An isolated mps structural gene which codes for the mps protein as described in claim 24.

26. The mps structural gene according to claim 25, which has been isolated and purified and consists of the DNA sequence as indicated by SEQ ID NO: 3.

* * * * *

SEQUENCE LISTING

<160> NUMBER OF SEQ ID NOS: 6

<210> SEQ ID NO 1
<211> LENGTH: 317
<212> TYPE: PRT
<213> ORGANISM: Magnetospirillum AMB-1

<400> SEQUENCE: 1

```
Met His Ile Leu Glu Phe Glu Lys Pro Ile Ala Glu Leu Glu Gly Lys
 1               5                  10                  15

Ile Glu Glu Leu Arg His Leu Ser Asp Gly Gly Asp Val Asn Ile Ala
            20                  25                  30

Asp Glu Val Ser Lys Leu Gln Ala Lys Val Asp Lys Leu Leu Arg Ser
        35                  40                  45

Thr Tyr Ala Lys Leu Thr Pro Trp Gln Lys Thr Gln Val Ala Arg His
    50                  55                  60

Pro Glu Arg Pro His Thr Leu Ala Tyr Ile Ser Thr Leu Ile Glu Asp
65                  70                  75                  80

Phe Thr Pro Leu Ala Gly Asp Arg Ala Phe Ala Glu Asp Glu Ala Ile
                85                  90                  95

Ile Gly Gly Leu Gly Arg Phe Arg Ala Ala Ser Val Met Ile Ile Gly
            100                 105                 110

His Glu Lys Gly His Asp Thr Glu Thr Arg Leu Lys His Asn Phe Gly
        115                 120                 125

Met Ala Lys Pro Glu Gly Tyr Arg Lys Ala Lys Arg Leu Met Glu Met
    130                 135                 140

Ala Asp His Phe Gln Val Pro Ile Ile Thr Leu Val Asp Thr Ala Gly
145                 150                 155                 160

Ala Tyr Pro Gly Val Asp Ala Glu Ala Arg Gly Gln Ala Glu Ala Ile
                165                 170                 175

Ala Arg Ser Ile Glu Thr Cys Leu Asn Val Arg Val Pro Leu Val Ser
            180                 185                 190

Val Ile Ile Gly Glu Gly Gly Ser Gly Gly Ala Ile Ala Leu Ala Thr
        195                 200                 205
```

```
Gly Asn Thr Val Leu Met Leu Glu His Ala Ile Tyr Ser Val Ile Ser
    210                 215                 220

Pro Glu Gly Cys Ala Ser Ile Leu Trp Arg Ser Ala Glu Asn Ala Lys
225                 230                 235                 240

Asp Ala Ala Glu Gln Leu Arg Leu Thr Ala Gln Asp Leu His Lys Leu
                245                 250                 255

Ser Ile Ile Asp Ser Val Val Pro Glu Pro Met Gly Gly Ala His Arg
                260                 265                 270

Asn Pro Asp Leu Met Met Gln Thr Leu Ser Met Ala Leu Asp Ser Ala
            275                 280                 285

Leu Arg Asp Leu Ser Gly Leu Asp Gly Gly Val Leu Arg Ala Arg Arg
    290                 295                 300

Arg Glu Lys Phe Leu Glu Met Gly Arg Ala Gly Leu Ser
305                 310                 315
```

<210> SEQ ID NO 2
<211> LENGTH: 954
<212> TYPE: DNA
<213> ORGANISM: Magnetospirillum AMB-1
<220> FEATURE:
<221> NAME/KEY: gene
<222> LOCATION: (217)..(702)
<223> OTHER INFORMATION: Predicted region encoding membrane bound
      portion of the mps gene product. "n" is any of a, t, c or g.

<400> SEQUENCE: 2

```
atgcayathy tngarttyga raarccnath gcngarytng arggnaarat hgargarytn      60
mgncayytnw sngayggngg ngaygtnaay athgcngayg argtnwsnaa rytncargcn     120
aargtngaya arytnytnmg nwsnacntay gcnaarytna cnccntggca raaracncar     180
gtngcnmgnc ayccngarmg nccncayacn ytngcntaya thwsnacnyt nathgargay     240
ttyacnccny tngcnggnga ymgngcntty gcngargayg argcnathat hggnggnytn     300
ggnmgnttym gngcngcnws ngtnatgath athggncayg araarggnca ygayacngar     360
acnmgnytna arcayaaytt yggnatggcn aarccngarg gntaymgnaa rgcnaarmgn     420
ytnatggara tggcngayca yttycargtn ccnathatha cnytngtnga yacngcnggn     480
gcntayccng gngtngaygc ngargcnmgn ggncargcng argcnathgc nmgnwsnath     540
garacntgyy tnaaygtnmg ngtnccnytn gtnwsngtna thathggnga rggnggnwsn     600
ggnggngcna thgcnytngc nacnggnaay acngtnytna tgytngarca ygcnathtay     660
wsngtnathw snccngargg ntgygcnwsn athytntggm gnwsngcnga raaygcnaar     720
gaygcngcng arcarytnmg nytnacngcn cargayytnc ayaarytnws nathathgay     780
wsngtngtnc cngarccnat gggnggngcn caymgnaayc cngayytnat gatgcaracn     840
ytnwsnatgg cnytngayws ngcnytnmgn gayytnwsng gnytngaygg nggngtnytn     900
mgngcnmgnm gnmgngaraa rttyytngar atgggnmgng cnggnytnws ntrr          954
```

<210> SEQ ID NO 3
<211> LENGTH: 954
<212> TYPE: DNA
<213> ORGANISM: Magnetospirillum AMB-1
<220> FEATURE:
<221> NAME/KEY: gene
<222> LOCATION: (217)..(702)
<223> OTHER INFORMATION: Sequence encoding membrane bound portion of mps
      structural gene product.

<400> SEQUENCE: 3

```
atgcatatcc ttgaattcga aaagcccatc gccgagctcg aggcaagat tgaggagctg       60
```

```
aggcacctgt ccgatggcgg cgacgtcaac atcgccgacg aggtgtccaa gctccaggcc      120
aaggtcgaca gctgctgcg ctcgacctac gccaagctca cgccgtggca aaagacgcag       180
gtggcccgcc accggagcg tccgcacacg ctggcctata tctcgacgct gatcgaggac       240
ttcacgccgc tggccggaga ccgcgccttc gccgaggacg aggccatcat cggcggcctg      300
ggccgtttcc gcgcggcttc ggtgatgatc atcggccacg agaagggcca cgacaccgaa      360
acccggctga agcacaattt cggcatggcc aagcccgagg ctatcgcaa ggccaagcgc       420 ctgatggaaa tggccgacca tttccaggtg cccatcatca ccctggtgga cactgccggc      480
gcctatcccg gcgtcgacgc cgaggcgcgg ggccaggcgg aggccatcgc ccgctccatc      540
gagacctgcc tgaacgttcg cgtgccgctg gtctcggtga tcatcggcga aggcggctcg      600
ggcggcgcca tcgccctggc caccggcaat accgtcctga tgctcgaaca cgccatctat      660
tcggtgatca gccccgaggg ctgcgcctcg atcctgtggc gctcggccga gaacgccaag      720
gacgccgccg aacagctgcg ccttaccgcc caggacctgc acaagctcag catcatcgat      780
tcggtggtgc ccgagcccat gggcggcgcc atcgcaatc ccgacctgat gatgcaaacc       840
ctgtccatgg cgctggattc ggcgctgcgc gacctgtcgg gcctggacgg cggcgtgctg      900
cgcgcccgcc gtcgcgagaa attcctggag atgggcgggg cgggcctgtc gtga            954
```

<210> SEQ ID NO 4
<211> LENGTH: 434
<212> TYPE: PRT
<213> ORGANISM: Magnetospirillum
<220> FEATURE:
<221> NAME/KEY: TRANSMEM
<222> LOCATION: (7)..(380)
<223> OTHER INFORMATION: Membrane bound region of mag A protein.

<400> SEQUENCE: 4

```
Met Glu Leu His His Pro Glu Leu Thr Tyr Ala Ala Ile Val Ala Leu
  1               5                  10                  15

Ala Ala Val Leu Cys Gly Gly Met Met Thr Arg Leu Lys Gln Pro Ala
             20                  25                  30

Val Val Gly Tyr Ile Leu Ala Gly Val Val Leu Gly Pro Ser Gly Phe
         35                  40                  45

Gly Leu Val Ser Asn Arg Asp Ala Val Ala Thr Leu Ala Glu Phe Gly
     50                  55                  60

Val Leu Met Leu Leu Phe Val Ile Gly Met Lys Leu Asp Ile Ile Arg
 65                  70                  75                  80

Phe Leu Glu Val Trp Lys Thr Ala Ile Phe Thr Thr Val Leu Gln Ile
                 85                  90                  95

Ala Gly Ser Val Gly Thr Ala Leu Leu Leu Arg His Gly Leu Gly Trp
            100                 105                 110

Ser Leu Gly Leu Ala Val Val Leu Gly Cys Ala Val Ala Val Ser Ser
        115                 120                 125

Thr Ala Val Val Ile Lys Val Leu Glu Ser Ser Asp Glu Leu Asp Thr
    130                 135                 140

Pro Val Gly Arg Thr Thr Leu Gly Ile Leu Ile Ala Gln Asp Met Ala
145                 150                 155                 160

Val Val Pro Met Met Leu Val Leu Glu Ser Phe Glu Thr Lys Ala Leu
                165                 170                 175

Leu Pro Ala Asp Met Ala Arg Val Val Leu Ser Val Leu Phe Leu Val
            180                 185                 190
```

```
Leu Leu Phe Trp Trp Leu Ser Lys Arg Arg Ile Asp Leu Pro Ile Thr
            195                 200                 205
Ala Arg Leu Ser Arg Asp Ser Asp Leu Ala Thr Leu Ser Thr Leu Ala
        210                 215                 220
Trp Cys Phe Gly Thr Ala Ala Ile Ser Gly Val Leu Asp Leu Ser Pro
225                 230                 235                 240
Ala Tyr Gly Ala Phe Leu Gly Gly Val Val Leu Gly Asn Ser Ala Gln
                245                 250                 255
Arg Asp Met Leu Leu Lys Arg Ala Gln Pro Ile Gly Ser Val Leu Leu
            260                 265                 270
Met Val Phe Phe Leu Ser Ile Gly Leu Leu Leu Asp Phe Lys Phe Ile
        275                 280                 285
Trp Lys Asn Leu Gly Thr Val Leu Thr Leu Leu Ala Met Val Thr Leu
290                 295                 300
Phe Lys Thr Ala Leu Asn Val Thr Ala Leu Arg Leu Ala Arg Gln Asp
305                 310                 315                 320
Trp Pro Ser Ala Phe Leu Ala Gly Val Ala Leu Ala Gln Ile Gly Glu
                325                 330                 335
Phe Ser Phe Leu Leu Ala Glu Thr Gly Lys Ala Val Lys Leu Ile Ser
            340                 345                 350
Ala Gln Glu Thr Lys Leu Val Val Ala Val Thr Val Leu Ser Leu Val
        355                 360                 365
Leu Ser Pro Phe Trp Leu Phe Thr Met Arg Arg Met His Arg Val Ala
370                 375                 380
Ala Val His Val His Ser Phe Arg Asp Leu Val Thr Arg Leu Tyr Gly
385                 390                 395                 400
Asp Glu Ala Arg Ala Phe Ala Arg Thr Ala Arg Arg Ala Arg Val Leu
                405                 410                 415
Val Arg Arg Gly Ser Trp Arg Asp Asp Pro Asn Ala Gly Pro Gly Ser
            420                 425                 430
Gly Ile
```

<210> SEQ ID NO 5
<211> LENGTH: 1302
<212> TYPE: DNA
<213> ORGANISM: Magnetospirillum AMB-1
<220> FEATURE:
<221> NAME/KEY: gene
<222> LOCATION: (1)..(1302)
<223> OTHER INFORMATION: Genomic DNA sequence encoding mag A gene.

<400> SEQUENCE: 5

| | | | | |
|---|---|---|---|---|
| atggaactgc atcatcccga actgacctat gccgccatcg tcgccctggc cgccgtgctg | | | | 60 |
| tgcggcggga tgatgacgcg cctgaagcag ccggccgtcg tcggctacat cctggcgggg | | | | 120 |
| gtggtgctgg acccagcggg cttcgggctg gtgagcaacc gcgacgccgt ggccaccctg | | | | 180 |
| gccgagttcg gcgtgctgat gctgctgttc gtcatcggca tgaagctgga catcatccgc | | | | 240 |
| tttctcgaag tgtggaagac ggccatcttc accacggttc tgcagatcgc cggcagcgtg | | | | 300 |
| ggcacggccc tgctgctgcg tcacggcctg gctggagcc tggggctggc ggtggtgctg | | | | 360 |
| ggctgtgccg tggcggtgtc gtccaccgcc gtagtgatca aggtgctgga atcctcggac | | | | 420 |
| gagctggaca cgccggtcgg ccgcaccacc cttggcatcc tgatcgccca ggacatggcg | | | | 480 |
| gtggtgccca tgatgctggt gctggaatcc ttcgagacca aggcgctgct gcccgccgac | | | | 540 |
| atggcccggg tggtgctgtc ggtgctgttc ctggtgctgc tgttctggtg gctgtccaag | | | | 600 |
| cgccgcatcg acctgccgat caccgcccgg cttccccgcg attctgacct tgccaccctg | | | | 660 |

```
tcgaccctgg cctggtgttt cggcaccgcc gccatctccg gcgtgctgga cttgtcgccg    720
gcctatggcg ccttcctggg cggcgtggtg ctgggcaatt ccgcccagcg cgacatgctg    780
ttgaagcgtg cccagcccat cggcagcgtg ctgctgatgg tgttcttcct gtccatcggg    840
ctgctgctcg acttcaagtt catctggaag aatctgggca ccgttctcac cctgctggcc    900
atggtgaccc tgttcaagac ggcgctgaac gtcacgcgc tgcgcctggc gcggcaggac     960
tgcccagcg ccttcctggc cggcgtggcc ctggcccaga tcggcgagtt ctcgttcctg    1020
ctggccgaga ccggcaaggc ggtcaagctg atcagcgccc aggagaccaa gctggtggtg   1080
gcggtcaccg tgctgtccct ggtgctgtcg ccgttctggc tgttcaccat gcggcgcatg   1140
caccgggtgg cggcggtgca tgtccattcg ttccgcgatc tggtcacgcg gctgtatggc   1200
gacgaggccc gcgctttcgc ccgcaccgcg cggcgggccc gtgtgctggt gcggcgtggt   1260
tcctggaggg atgaccccaa tgccggacct ggctctggaa tt                      1302

<210> SEQ ID NO 6
<211> LENGTH: 1302
<212> TYPE: DNA
<213> ORGANISM: Magnetospirillum
<220> FEATURE:
<221> NAME/KEY: gene
<222> LOCATION: (1)..(1302)
<223> OTHER INFORMATION: Predicted sequence of mag A structural gene.
      "n" is any of a, t, g or c.

<400> SEQUENCE: 6
atggarytnc aycayccnga rytnacntay gcngcnathg tngcnytngc ngcngtnytn    60
tgyggnggna tgatgacnmg nytnaarcar ccngcngtng tnggntayat hytngcgggn   120
gtngtnytng gnccnwsngg nttyggnytn gtnwsnaaym gngaygcngt ngcnacnytn   180
gcngarttyg gngtnytnat gytnytntty gtnathggna tgaarytnga yathathmgn   240
ttyytngarg tntggaaarac ngcnathtty acnacngtny tncarathgc nggnwsngtn   300
ggnacngcny tnytnytnmg ncayggnytn ggntggwsny tnggnytngc ngtngtnytn   360
ggntgygcng tngcngtnws nwsnacngcn gtngtnatha argtnytnga rwsnwsngay   420
garytngaya cnccngtngg nmgnacnacn ytnggnathy tnathgcnca rgayatggcn   480
gtngtnccna tgatgytngt nytngarwsn ttygaracna argcnytnyt nccgcngay    540
atggcnmgng tngtnytnws ngtnytntty ytngtnytny tnttytggtg gytnwsnaar   600
mgnmgnathg ayytnccnat hacngcnmgn ytnwsnmgng aywsngayyt ngcnacnytn   660
wsnacnytng cntggtgytt yggnacngcn gcnathwsng gntnytnga yytnwsnccn    720
gcntayggng cnttyytngg nggngtngtn ytnggnaayw sngcncarmg ngayatgytn   780
ytnaarmgng cncarccnat hggnwsngtn ytnytnatgg tnttyttyyt nwsnathggn   840
ytnytnytng ayttyaartt yathtggaar aayytnggna cngtnytnac nytnytngcn   900
atggtnacny tnttyaarac ngcnytnaay gtnacngcny tnmgnytngc nmgncargay   960
tggccnwsng cnttyytngc nggngtngcn ytngcncara thggngartt ywsnttyytn  1020
ytngcngara cnggnaargc ngtnaarytn athwsngcnc argaracnaa rytngtngtn  1080
gcngtnacng tnytnwsnyt ngtnytnwsn ccnttytggy tnttyacnat gmgnmgnatg  1140
caymgngtng cngcngtnca ygtncaywsn ttymgngayy tngtnacnmg nytntayggn  1200
gaygargcnm gngcnttygc nmgnacngcn mgnmgngcnm gngtnytngt nmgnmgnggn  1260
wsntggmgng aygayccnaa ygcnggnccn ggnwsnggna th                     1302
```